(12) United States Patent
Helbley et al.

(10) Patent No.: US 11,079,316 B2
(45) Date of Patent: Aug. 3, 2021

(54) INTRINSICALLY SAFE SPECTROSCOPIC ANALYZER

(71) Applicant: SpectraSensors, Inc., Rancho Cucamonga, CA (US)

(72) Inventors: Keith Benjamin Helbley, Rancho Cucamonga, CA (US); Juergen Dessecker, Rancho Cucamonga, CA (US); Harald Mueller, Fulda (DE); Nikolai Fink, Aesch (CH); William Boyle, Rancho Cucamonga, CA (US); Peter Dorn, Rancho Cucamonga, CA (US); Paulo Silva, Rancho Cucamonga, CA (US)

(73) Assignee: SpectraSensors, Inc., Rancho Cucamonga, CA (US)

(*) Notice: Subject to any disclaimer, the term of this patent is extended or adjusted under 35 U.S.C. 154(b) by 0 days.

(21) Appl. No.: 15/065,783

(22) Filed: Mar. 9, 2016

(65) Prior Publication Data
US 2016/0266034 A1    Sep. 15, 2016

Related U.S. Application Data

(60) Provisional application No. 62/130,463, filed on Mar. 9, 2015.

(51) Int. Cl.
*G01N 21/31* (2006.01)
*G01N 21/3504* (2014.01)
(Continued)

(52) U.S. Cl.
CPC ............ *G01N 21/31* (2013.01); *G01J 1/4257* (2013.01); *G01N 21/3504* (2013.01);
(Continued)

(58) Field of Classification Search
CPC .............. G01N 21/31; G01N 33/0004; G01N 21/3504; G01N 21/39; G01N 2201/0612;
(Continued)

(56) References Cited

U.S. PATENT DOCUMENTS 4,323,777 A * 4/1982 Baskins ............. G01N 33/0047
250/338.5
5,252,060 A * 10/1993 McKinnon ............. F23N 5/003
431/12
(Continued)

FOREIGN PATENT DOCUMENTS

CN         1702584 A      11/2005
CN       201414081 Y       2/2010
(Continued)

OTHER PUBLICATIONS

McGeehin, Peter. *Optical Techniques in Industrial Measurement: Safety in Hazardous Environments*. N.p.: European Commission, 1994. BCR Information: Applied Metrology. Web. May 19, 2016.
(Continued)

*Primary Examiner* — Mohamed K Amara
(74) *Attorney, Agent, or Firm* — Kelly J. Smith; Endress+Hauser (USA) Holding Inc.

(57) ABSTRACT

A laser spectrometer can be operated for analysis of one or more analytes present in a combustible gas mixture. The spectrometer can include one or more features that enable intrinsically safe operation. In other words, electrical, electronic, thermal, and/or optical energy sources can be limited within an hazardous are of the spectrometer where it is possible for an explosive gas mixture to exist. Methods, systems, articles and the like are described.

23 Claims, 11 Drawing Sheets

(51) Int. Cl.
  *G01N 21/39*    (2006.01)
  *G01J 1/42*     (2006.01)
  *G01N 33/00*    (2006.01)
  *H02H 9/00*     (2006.01)

(52) U.S. Cl.
  CPC ......... *G01N 21/39* (2013.01); *G01N 33/0004* (2013.01); *G01N 2201/0236* (2013.01); *G01N 2201/061* (2013.01); *G01N 2201/0612* (2013.01); *G01N 2201/127* (2013.01); *H02H 9/008* (2013.01)

(58) Field of Classification Search
  CPC ....... G01N 2201/061; G01N 2201/127; G01N 2201/0236; G01J 3/02; H02H 9/008
  See application file for complete search history.

(56) References Cited

U.S. PATENT DOCUMENTS

| | | | | |
|---|---|---|---|---|
| 5,828,307 | A * | 10/1998 | Washer | G01N 21/3504 340/632 |
| 6,182,497 | B1 * | 2/2001 | Krajci | G01N 33/0075 340/605 |
| 6,410,842 | B1 * | 6/2002 | McAlonan | H01L 35/00 136/242 |
| 7,058,099 | B2 * | 6/2006 | Stewart | H04B 10/504 372/18 |
| 7,229,436 | B2 * | 6/2007 | Stern | A45D 44/22 606/41 |
| 7,236,507 | B2 * | 6/2007 | Stewart | H04B 10/504 372/32 |
| 7,267,675 | B2 * | 9/2007 | Stern | A45D 44/22 606/31 |
| 7,269,191 | B2 * | 9/2007 | Stewart | H04B 10/07957 372/34 |
| 7,351,976 | B2 * | 4/2008 | Arno | G01J 3/32 250/343 |
| 7,359,643 | B2 * | 4/2008 | Aronson | G02B 6/4246 398/136 |
| 7,385,692 | B1 * | 6/2008 | Nguyen | G01J 3/02 356/301 |
| 7,634,197 | B2 * | 12/2009 | Nelson | H04B 10/504 372/33 |
| 7,705,988 | B2 * | 4/2010 | Richman | G01J 3/4338 356/437 |
| 8,085,301 | B2 * | 12/2011 | Hill, Jr. | G01J 3/0264 348/164 |
| 8,164,748 | B1 * | 4/2012 | Flanders | G01J 3/108 356/300 |
| 8,269,174 | B2 * | 9/2012 | Gardner | G01J 3/02 250/341.8 |
| 8,500,442 | B2 * | 8/2013 | Knittel | F23N 5/003 431/76 |
| 9,258,535 | B2 * | 2/2016 | Pool | H04N 5/2256 |
| 9,261,261 | B2 * | 2/2016 | Nishio | G01J 1/0271 |
| 9,513,204 | B2 * | 12/2016 | Paul | G01N 15/06 |
| 9,546,950 | B2 * | 1/2017 | Schachinger | G01N 21/31 |
| 9,568,418 | B1 * | 2/2017 | Hug | G01J 3/44 |
| 10,132,786 | B2 * | 11/2018 | Diekmann | G01N 33/0011 |
| 10,194,854 | B2 * | 2/2019 | Keating | A61B 5/201 |
| 2004/0080890 | A1 | 4/2004 | Ramsay et al. | |
| 2005/0247878 | A1 * | 11/2005 | Baschant | G01N 21/3504 250/343 |
| 2009/0019913 | A1 * | 1/2009 | Gu | G01N 33/0006 73/1.06 |
| 2011/0273708 | A1 * | 11/2011 | Tong | G01N 21/39 356/312 |
| 2014/0036257 | A1 | 2/2014 | Kramer et al. | |
| 2015/0068287 | A1 * | 3/2015 | Wilcox | G01M 3/22 73/40.5 R |
| 2015/0268416 | A1 * | 9/2015 | Coffey | G01D 11/00 250/227.11 |
| 2016/0356474 | A1 * | 12/2016 | Jayawardena | F21V 25/10 |
| 2018/0092540 | A1 * | 4/2018 | Panasyuk | G01J 3/0224 |

FOREIGN PATENT DOCUMENTS

| | | |
|---|---|---|
| CN | 101887009 A | 11/2010 |
| CN | 202256154 U | 5/2012 |
| CN | 202372491 U | 8/2012 |
| CN | 103364367 A | 10/2013 |
| CN | 204118765 U | 1/2015 |
| EP | 2317622 A1 | 5/2011 |

OTHER PUBLICATIONS

SICK AG. *TRANSIC100LP Laser Oxygen Transmitter*. Germany: SICK AG, 2015. Web. May 20, 2016.

* cited by examiner

INTRINSICALLY SAFE SPECTROSCOPIC ANALYZER

CROSS-REFERENCE TO RELATED APPLICATIONS

The current application claims priority to provisional application Ser. No. 62/130,463 filed Mar. 9, 2015, the disclosure of which is incorporated herein by reference in its entirety.

TECHNICAL FIELD

The subject matter described herein relates to spectroscopy-based analyzers, for example laser spectrometers used for analysis of one or more analytes, and specifically to improving the hazardous location safety of spectroscopy-based analyzers.

BACKGROUND

In an electronic instrument that is located in an atmosphere where there is a potential for an explosion or other incendiary hazards, eliminating such hazards can be desirable. Currently practiced approaches include making all the enclosures and interfaces to the hazardous atmosphere explosion proof. However doing so can be expensive and require addition of bulky and inconvenient components and structures to the instrument. In particular, an explosion proof enclosure that includes an optical window of very high quality to pass through a precision laser beam can be quite difficult to design and costly to manufacture.

Prevention or mitigation of a potential explosion must be considered any time an electrical or electronic instrument is placed in a hazardous environment. Typical approaches to mitigating potential explosion-related hazards can include flame-proof/explosion-proof housings, which are typically made from die-cast, heavy, and expensive aluminum boxes, which are designed to be sufficiently robust in construction contain and prevent propagation of an explosion and to generally resist fracture or distortion under internal pressures generated by an explosive event. Other methods include inert-gas purge and positive pressure differential systems (which can include static pressure, leakage compensation, and/or continuous dilution systems designed to maintain prevent generation of a potentially explosive environment around any electrically energized components), oil immersion, powder filling, encapsulation of energized components, and the like.

A frequently required hazardous location certification for a typical optical analyzer is a Canadian Standards Association (CSA) Division 1 certification, which is truly explosion proof, or its French counterparts: an ATEX (Appareils destinés à être utilisés en ATmosphères EXplosibles, from the French title of the 94/9/EC directive) Zone 0 or Zone 1 certification. In general, all such explosion or flame proof designs need to be tested and certified by one or more regulatory bodies. These certifications and tests typically need to be repeated multiple times to comply with various international hazardous location certifications, including but not limited to CSA (for US and Canada), ATEX (for Europe), IECEx (for Australia and other regions), GOST (for Russia and other countries of the former USSR), Inmetro for Brazil, and the like.

SUMMARY

In one aspect of the current subject matter, operating a laser spectrometer for analysis of one or more analytes present in a mixture containing at least one combustible gas. The operating includes providing electrical power to a plurality of components and optical power from a laser to a volume of the mixture. A hazardous area part of at least one of the plurality of components resides in a hazardous area of the spectrometer that may contain the mixture and that does not include at least one explosion mitigating structure. The method further includes limiting an optical power, electrical, electronic, and/or thermal ignition-causing parameter of the hazardous area part to less than a safety threshold to prevent occurrence of an ignition energy sufficient to ignite the combustible gas mixture. The optical power, electrical, electronic, and/or thermal ignition-causing parameter includes one or more of the optical power delivered from the laser to the volume of the mixture, an amount of particles exposed to radiation from the laser that has not been optical power limited, a current provided to the hazardous area part, a voltage provided to the hazardous area part, a temperature of the hazardous area part, and a stored energy of the hazardous area part. The method also further includes limiting the optical power, electrical, electronic, and/or thermal ignition-causing parameter for a non-hazardous area part of the at least one of the plurality of components. The non-hazardous area part resides in a non-hazardous area of the spectrometer that either cannot contain the mixture or that includes the at least one explosion mitigating structure.

In some variations, one or more of the following features can optionally be included in any feasible combination. For example, the limiting can include monitoring at least one of the optical power, the current, the voltage, the temperature, and the stored energy in or applied into the hazardous area. The plurality of components can include a laser, a photodetector, a temperature control device, a temperature sensor, a temperature thermistor, a pressure transducer, an optical power reduction device and a flow sensor.

The limiting can include limiting a voltage provided to at least one of the plurality of components to less than a minimum voltage capable of causing the ignition energy. In this example, a method can further include detecting that a voltage provided to at least one of the plurality of components is greater than or equal to the minimum voltage, and reducing the voltage by triggering a transistor and/or an electronic and/or an electro-mechanical circuit to increase an effective resistance. The limiting can further include use of at least one of a clamping zener diode, a fuse, an active power limiting circuit including an operational amplifier, and a voltage divider. The limiting can further include use of a fuse, and wherein the fuse includes a thermal fuse operable to prevent an over-temperature condition in the hazardous area.

The limiting can include a current provided to at least one of the plurality of components to less than a minimum current capable of causing the ignition energy sufficient to ignite the combustible gas mixture. The limiting of the current can include monitoring the current using at least one of a current monitoring circuit, an active power limiting circuit, and a current sensing resistor.

The limiting can include limiting a surface temperature of at least one of the plurality of components to less than a minimum temperature capable of causing the ignition energy sufficient to ignite the combustible gas mixture.

A method can further include detecting that at least one of the current, the voltage, and the temperature is greater than or equal to the threshold; and reducing the detected at least one of the current, the voltage, and the temperature to an amount that is less than the threshold.

The limiting can include reducing or cutting off voltage or current applied to at least one of the plurality of components. Alternatively or in addition, the limiting can include preventing power spikes using coupling capacitors and zener diodes to smooth current or voltage applied to at least one of the plurality of components. Limiting the optical power in the gas mixture can include passing radiation from the laser through an absorptive and/or reflective optical filter that reduces the optical power to less than a safety threshold.

A method can further include providing energy optically to the hazardous area part via a fiber optic cable. A fiber-coupled high efficiency laser diode can optionally provide and limit voltage or current to at least one of the plurality of components, and light delivered by a fiber optic cable can be converted into electric power provided to the plurality of components.

A method can also optionally include providing electric power to the plurality of components using a solar cell.

In an interrelated aspect, a laser spectrometer includes an enclosed hazardous area configured to contain a potentially combustible gas mixture to allow analysis of one or more analytes present in the combustible gas mixture; a plurality of components, a hazardous part of at least one of the plurality of components residing in the enclosed area; and electrical and/or computing hardware configured to perform operations. The operations include one or more of the features discussed above.

In optional variations, the plurality of components can include one or more of a laser, a photodetector, a temperature control device, a temperature sensor, a temperature thermistor, a pressure transducer, and a flow sensor. A laser spectrometer can further include a laser and an optical filter, and the limiting can include limiting the optical power by passing optical radiation emitted by the laser through the optical filter prior to the optical radiation encountering gas that may contain particles. The optical filter can be operable to limit the optical power of the optical radiation to less than a safety threshold sufficient to prevent occurrence of an ignition source exposed to the combustible gas mixture.

In yet another optional variation, a computer program product includes a machine-readable medium storing instructions that, when executed by at least one programmable processor, cause the at least one programmable processor to perform operations. The operations include operating a laser spectrometer for analysis of one or more analytes present in a mixture containing at least one combustible gas. The operating includes providing electrical power to a plurality of components and optical power from a laser to a volume of the mixture. A hazardous area part of at least one of the plurality of components resides in a hazardous area of the spectrometer that may contain the mixture and that does not include at least one explosion mitigating structure. The operations further include monitoring a status of an optical power, electrical, electronic, and/or thermal ignition-causing parameter in or applied into the hazardous area. The optical power, electrical, electronic, and/or thermal ignition-causing parameter includes one or more of the optical power delivered from the laser to the volume of the mixture, an amount of particles exposed to radiation from the laser that has not been optical power limited, a current provided to the hazardous area part, a voltage provided to the hazardous area part, a temperature of the hazardous area part, and a stored energy of the hazardous area part. The operations further include limiting the optical power, electrical, electronic, and/or thermal ignition-causing parameter of the laser spectrometer to less than a safety threshold to prevent occurrence of an ignition energy sufficient to ignite the combustible gas mixture.

Systems and methods consistent with this approach are described as well as articles that comprise a tangibly embodied machine-readable medium operable to cause one or more machines (e.g., computers, etc.) to result in operations described herein. Similarly, computer systems are also described that may include a processor and a memory coupled to the processor. The memory may include one or more programs that cause the processor to perform one or more of the operations described herein.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Figure 1:
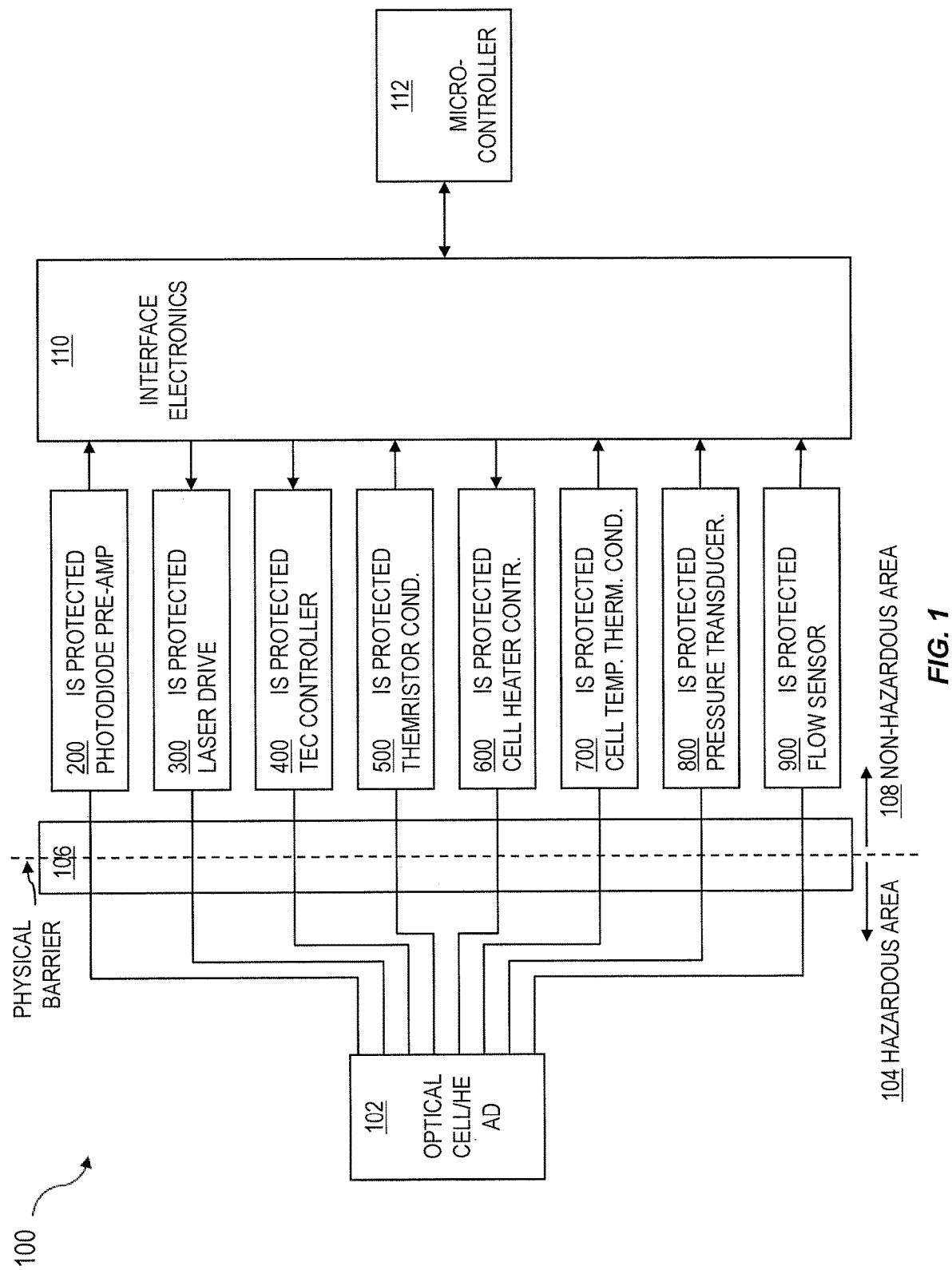
FIG. 1 shows an example schematic diagram illustrating hardware modules of a system for analyzing samples of a reactive or potentially explosive gas or gas mixture.

The subject matter described herein relates to providing safety circuits and components within the optical, electrical, and/or electronic circuits of modules attached to a sample cell of a spectroscopy-based analyzer. Spectroscopy-based analyzers (also referred to herein as spectrometers, laser spectrometers for analysis, and the like) and other like devices can be used to measure samples within hazardous gases, which as noted above can pose significant risks of explosions, incendiary hazards, or other flammability or combustion-related concerns when exposed to a spark or excess energy. Therefore, such analyzers and other like devices can be required to meet industry safety certifications, for example certifications such as CSA Divison1, ATEX Zone 0, ATEX Zone1, and the like, as required by a specific operating environment or commercial/industrial application. Complying with such certifications can be burdensome and expensive. Furthermore, beyond the various region-specific or industry-specific safety certifications, an intrinsically safe spectrometer, which can therefore require less stringent mitigation efforts to ensure safe operation, can be quite desirable. Currently available solutions generally do not provide approaches that meet one or more of these criteria.

To address these and potentially other issues with currently available solutions, one or more implementations of the current subject matter provide methods, systems, and the like that can, among other possible advantages, provide intrinsically safe configurations and techniques for use with electrical and/or electronic circuits driving modules within spectroscopy-based analyzers. Such configurations and techniques can make the modules, and thus the spectroscopy-based analyzer itself, "intrinsically safe." An intrinsically safe design for a spectrometer can provide significant cost advantages, improved safety, and better world wide applicability of a spectrometer, by eliminating the need for testing by multiple certification agencies, and especially by eliminating the need to use heavy, expensive, bulky enclosures to achieve CSA Divison1 and ATEX Zone1 certification.

Achieving Div1/Zone1 or other certification can require all barrier surfaces separating electrical components from hazardous gas to be sized to provide sufficient pathlength for a flame front to be cooled to below the incendiary point of any flammable gas. Explosion tests for hazardous location certification can typically be performed by striking an acetylene explosion inside the compartment containing the electrical or electronic components. An intrinsically safe electronic design can prevent these design complications and tests by maintaining all surface temperatures of components below incendiary levels and/or by limiting power levels by limiting voltages, stored energy and maximum current capability of the circuits to conditions below the minimum energy required to ignite a spark. Such a design can dramatically improve safety and applicability of spectrometers, for example tunable diode laser (TDL) spectrometers, and can reduce significant certification costs and the added cost and size for flame path cooling designs and can also eliminate or reduce costs for heavy, bulky enclosures needed to achieve Div1/Zone1 certifications.

Consistent with implementations of the current subject matter, a spectroscopy-based analyzer can include one or more features capable of improving the analyzer's resistance to explosion hazards. In some examples, a compact and closed configuration can include all parts of the system being directly connected or coupled to each other, and an external system interface to the outside being explosion proof. Other examples can include a split (i.e., remote) configuration that need not include intrinsically safe design techniques. In such examples, an analyzer can be split into multiple parts, for example, with a separate electronics compartment and a separate compartment for the optical module. In this configuration, all compartments are desirably explosion proof, and the connection between the different compartments is desirably wired in a conduit or other protected enclosure. This approach can be cost-prohibitive in many cases and can require significantly higher efforts for achieving desirable safety certifications.

Still other examples can include a split (i.e., remote) configuration that incorporates intrinsically safe features. Such an analyzer system can be split into multiple parts as was described in the second configuration. However, the use of conduits can advantageously be avoided because all connections can be intrinsically safe, which can reduce the cost and can enable the layout of components in a sample conditioning system associated with the analyzer to be much more flexible. In such a "split" configuration, components of the spectrometer can include hazardous area parts that are located within a "hazardous area" of the spectrometer and other, non-hazardous area parts located within a "non-hazardous area." The hazardous area of the spectrometer may contain the combustible mixture and generally does not include at least one explosion mitigating structure (e.g. an explosion proof enclosure, explosion propagation prevention devices, etc.). The non-hazardous area generally include an explosion proof container or other features that prevent entry of potentially combustible gases. The optical power, electrical, electronic, and/or thermal ignition-causing parameters need not be limited in the non-hazardous area.

To make the spectrometer intrinsically safe, an optical power, electrical, electronic, and/or thermal ignition-causing parameter of the hazardous area parts can advantageously be limited to less than a safety threshold to prevent occurrence of an ignition energy sufficient to ignite the combustible gas mixture. The optical power, electrical, electronic, and/or thermal ignition-causing parameter can include one or more (or optionally all) of the optical power delivered from the laser to the volume of the mixture, an amount of particles exposed to radiation from the laser that has not been optical power limited, a current provided to the hazardous area part, a voltage provided to the hazardous area part, a temperature of the hazardous area part, and a stored energy of the hazardous area part.

FIG. 1 shows an example schematic diagram illustrating hardware modules of a system 100 for analyzing samples of a reactive or potentially explosive gas or gas mixture. The system 100 can represent at least some elements within a spectroscopy-based analyzer. An optical head 102, which can include a laser or other radiation source, one or more lenses or reflectors, etc., can be exposed to a hazardous area 104 where a reactive or potentially explosive gas is contained. A physical barrier 106 can seal the remainder of the components residing in the non-hazardous or "safe" area 108, from the hazardous area 104, by preventing gas from the hazardous area 104 from penetrating into the non-hazardous area 108 and/or by enclosing the non-hazardous area 108 is an explosion-proof housing that mitigates explosion hazards even if gas from the hazardous area does penetrate into the non-hazardous area 108. In this manner, a spark, excess energy condition, or other potential ignition source in the non-hazardous area 108 can be prevented from causing explosions or other combustion events in the hazardous area 104. The optical head 102 can interface with and be connected to one or more hardware modules, which can include one or more of an intrinsically safe (IS) photodiode preamplification module 200, an intrinsically safe laser diode driving current module 300 (i.e., laser diode driver), one or more intrinsically safe cooling power modules 400 (e.g., for powering one or more thermoelectric coolers or the like for controlling a temperature of a semiconductor laser, a photodetector, or the like), an intrinsically safe temperature monitoring module 500 (e.g., for controlling a thermistor temperature sensor or the like for monitoring a temperature of a semiconductor laser, a photodetector, or the like), an intrinsically safe heater controller module 600, an intrinsically safe temperature thermistor conditioner module 700, an intrinsically safe pressure transducer module 800, and an intrinsically safe flow sensor module 900 as illustrated in further detail in FIGS. 2-9, respectively.

It will be understood that one or more of the modules 200, 300, 400, 500, 600, 700, 800, 900 shown in FIG. 1 and discussed in greater detail below can be included or omitted from a spectrometer system based on the presence or absence of other safety measures for preventing an explosion. For example, some implementations of the current subject matter may omit an intrinsically safe cell heater controller module 600 and instead encapsulate all electrical leads for supplying current to an optical cell heater unit within conduit or other explosion-proof containers. Such an approach may be desirable for a relatively large cell that requires significant heating (and associated heater current) t be maintained at a target temperature. The energy usage overhead of maintaining an intrinsically safe circuit for this part of a spectrometer may be large enough to make the physical explosion mitigation structures economically viable. On the other hand, in an implementation in which an optical cell has a relatively small volume (and therefore a relatively low heating load), or alternatively in an implementation in which conduits and other explosion protection apparatus is undesirable or not as economically feasible, use of the intrinsically safe cell heater controller module 600 shown in FIG. 6 or a comparable replacement can be desirable. Similar considerations apply to all of the modules 200, 300, 400, 500, 600, 700, 800, 900 discussed in relation to FIG. 1-9. Each of these modules can be implemented or not implemented in a spectrometer to the extent that avoidance of other explosion-resistant or explosion preventative measures are not desirable for any reason.

Notably, the specific arrangement of the system 100 as shown in FIG. 1, and particularly, the inclusion of the various modules 200-900 therein, are depicted as such for demonstration purposes only. Similarly, the specific circuit and/or component arrangements as shown in FIGS. 2-9 are depicted as such for demonstration purposes only. Thus, the depicted arrangements should not be treated as limiting the scope of the current subject matter, but merely as illustrations further to explanations of possible implementations. The embodiments as depicted in the figures or described herein can be altered, as would be understood by a person of ordinary skill in the art, in any manner suitable within the scope of the present claims. Moreover, the component values (e.g., voltages, currents, etc.) associated with components in the modules 200-900 can be adjusted to define sensitivities, thresholds, current and voltage altering functionalities, such as current and voltage limiting, reducing, cutoff, and smoothing, and the like, as would be understood by a person of ordinary skill in the art, in any manner suitable within the scope of the present claims.

The hardware modules 200-900 can be controlled by a microcontroller 112, and can interface with the microcontroller 112 and other electronic components via an electronics interface 110. These hardware modules can interface to optical components on the optical head 102, and can provide one or more functions, such as for example, providing photodiode preamplification, driving current to a laser diode, controlling the power to a thermoelectric cooler (TEC), controlling a thermistor temperature sensor, and the like. The hardware modules 200-900 can also limit the energy available in the area where the hazardous atmosphere exists (e.g., on the hazardous area 104) so that no source of ignition is available (e.g., a spark, a hot surface, etc.).

Limiting the energy in the hazardous area 104 can include limiting the power by limiting the current and/or voltage, as well as the temperature that can be exposed to the hazardous area 104 from components and circuitry within the non-hazardous area 108 that can interface with the optical head 102. Each of the photodiode preamplification module 200, the laser diode driving current module 300 (i.e., laser diode driver), the one or more cooling power modules 400, the one or more temperature monitoring modules 500, the heater controller module 600, the temperature thermistor conditioner module 700, the pressure transducer module 800, and the flow sensor module 900, can include circuitry and electronic components capable of performing all or some of the power-, voltage-, current-, and temperature-limiting functions described herein. Clamping zener diodes, active circuitry monitoring, limiting or cutting off specific voltages, among other possible structures or approaches, can be employed for limiting the power and voltage at the optical head 102. Strategic resistor placement, fuses, active circuitry monitoring, limiting or cutting off current, or current sensing resistors, among other possible structures or approaches, can be employed for limiting the power and current at the optical head 102. These methodologies, along with the use of wired thermal fuses or other possible structures or approaches, can control and limit heat at the optical head 102. Limiting the power, voltages, currents, and component surface temperatures at the optical head 102 can increase safety and reduce the risk of combustion or explosion such that the system 100, along with its hardware modules and components, can qualify as "intrinsically safe."

In order to qualify as intrinsically safe, consistent with implementations of the current subject matter, electrical connections passing from a non-hazardous or safe area 108 to a hazardous area 104 in a spectrometry-based analyzer are advantageously energy limited. Non-limiting examples of limits and other criteria for complying with the international standards are contained in the latest versions of the IEC 60079-11 standard, the IEC 60079-25 standard, and other IEC 60079-XX standards.

Figure 2:
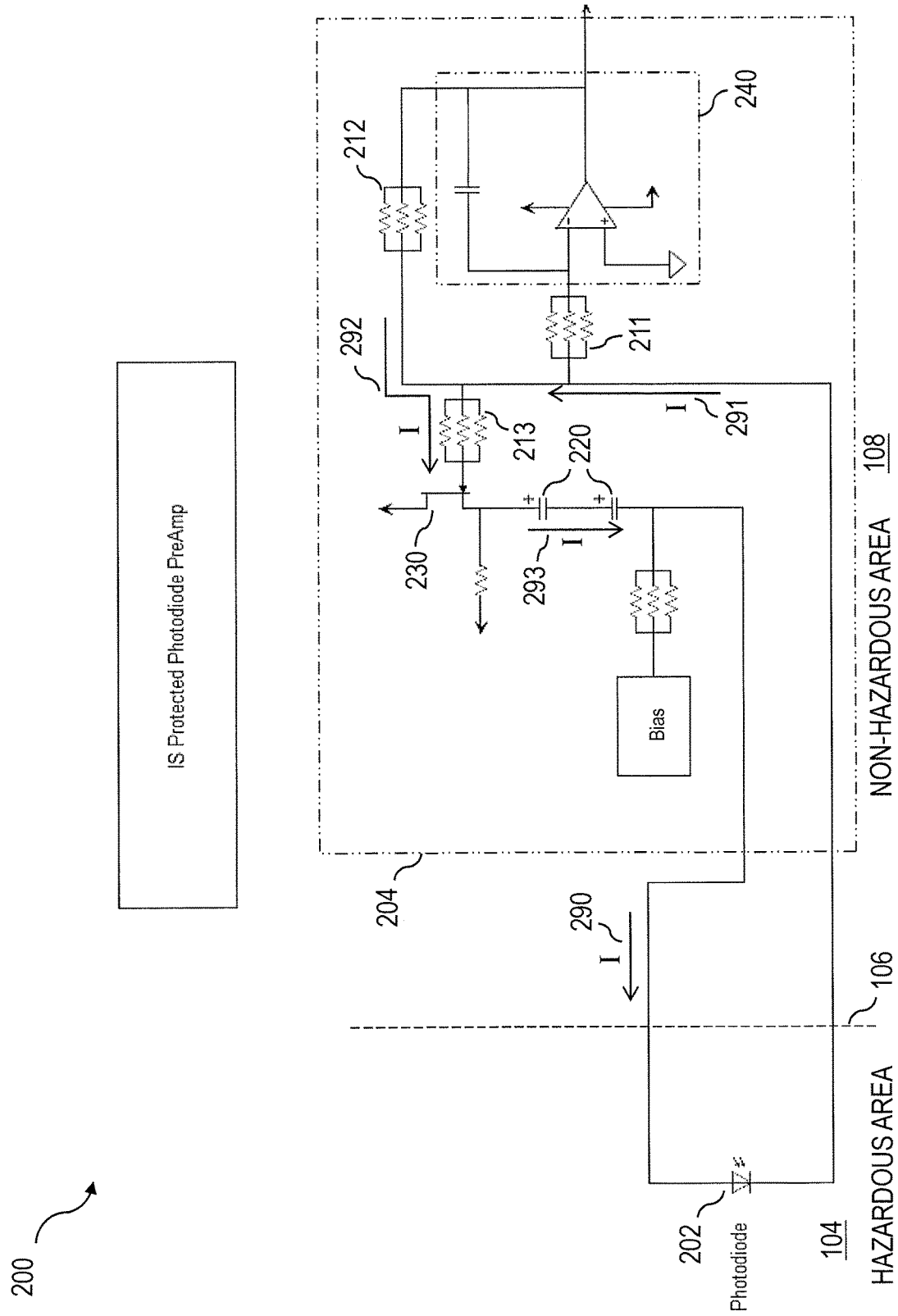
FIG. 2 shows a schematic diagram illustrating examples of features of a protected photodiode preamplification module that can be included in the system for analyzing samples of a reactive or potentially explosive gas or gas mixture, and the circuit design and components for making this module intrinsically safe.

FIG. 2 shows a schematic diagram illustrating example features of a protected photodiode preamplification module 200 consistent with the system 100 shown in FIG. 1, and circuit design and components that can be used to make such a module intrinsically safe consistent with implementations of the current subject matter. A photodiode 202 can reside in the hazardous area 104, and a photodiode protecting circuit 204 can reside in the non-hazardous area 108, separated by the physical barrier 106. The photodiode protecting circuit 204 can limit or reduce (or, in some implementations of the current subject matter, monitor and limit or reduce) the current at an output circuit branch 290 that can be fed into the photodiode 202. Providing a low and controlled current from the output circuit branch 290 to the photodiode 202 without risk of spiking can enable the photodiode 202 to qualify as intrinsically safe. Various resistors 211, 212, 213, 214 and capacitors 220 can be strategically connected within the photodiode protecting circuit 204 to provide one or more safety-related functions.

The photodiode protecting circuit 204 can be configured such that the currents within the photodiode protecting circuit 204 can be considered intrinsically safe, and such that the photodiode protecting circuit 204 can perform one or more of monitoring, limiting, and reducing current at the output circuit branch 290 entering into the photodiode 202 in the following manner. For example, the current at the output circuit branch 290 has the same value as the current at a first circuit branch 291. The magnitude of current at the first circuit branch 291 can be monitored across the first resistor 211 using a current monitoring circuit 240. The current monitoring circuit 240 can include operational amplifier feedback functionality. Adjusting the resistance of the first resistor 211 can adjust and determine the sensitivity of the current monitoring circuit 240. As the monitored current at the first circuit branch 291 rises, so does the feedback current at a second circuit branch 292 across the second resistor 212 and the third resistor 213. If the feedback current at the second circuit branch 292 rises beyond a threshold determined by a transistor 230, the transistor 230 can limit, reduce, or completely cut-off feedback current at the second circuit branch 292, such that the magnitude of current at a third circuit branch 293 can be maintained below a threshold safe value. As described herein, the threshold may be variously defined. For example, the threshold may be a minimum current capable of causing ignition energy sufficient to ignite a potentially combustible gas mixture in the hazardous area 104. Furthermore, the capacitors 220 can be alternate current (AC) coupling capacitors that can allow AC current to pass through while blocking out direct current (DC), as well as can smooth out current at the third circuit branch 293 before it becomes current at the output circuit branch 290 that is fed into the photodiode 202.

Figure 3:
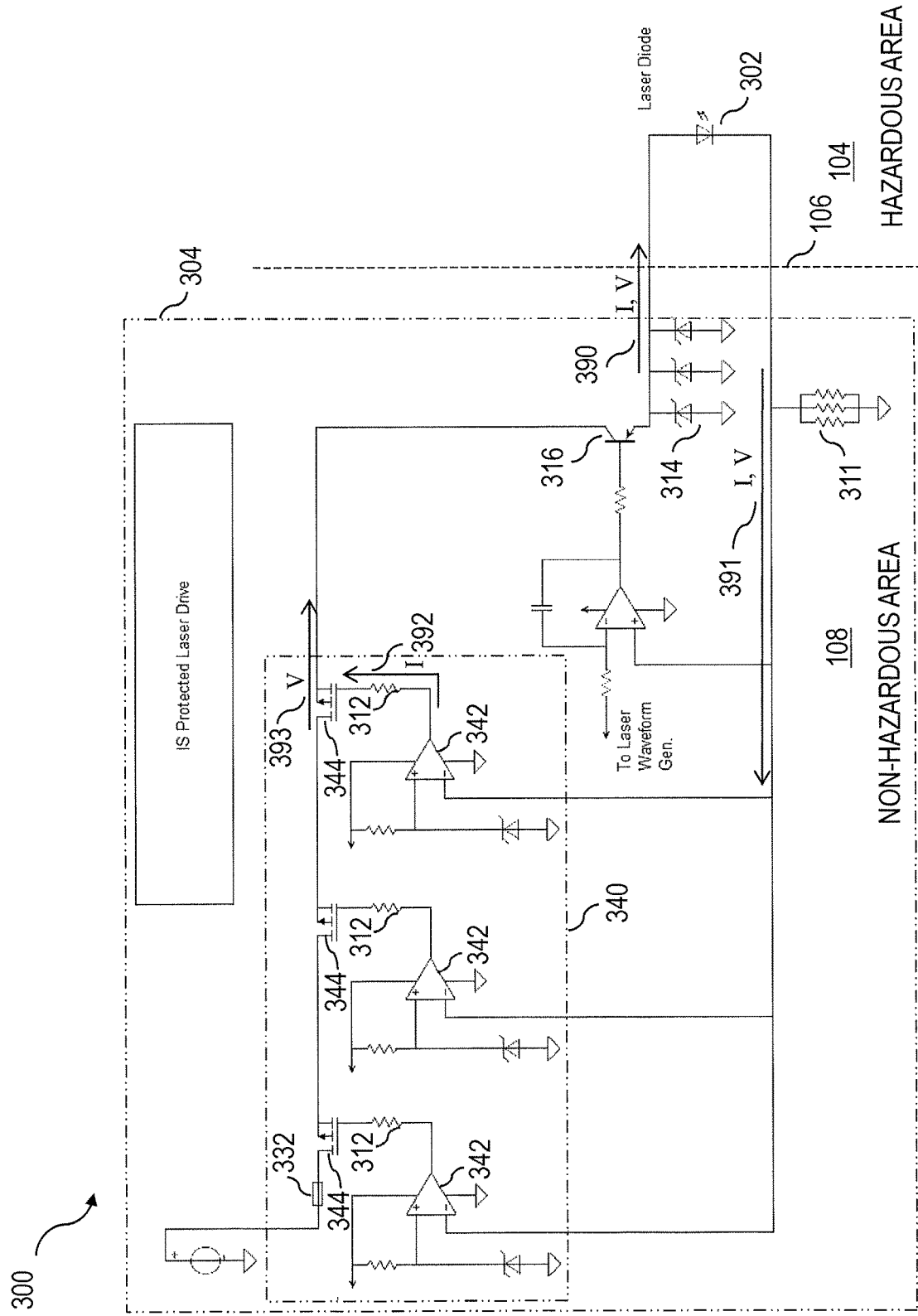
FIG. 3 shows a diagram illustrating examples of features of a protected laser driving module that can be included in the system for analyzing samples of a reactive or potentially explosive gas or gas mixture, and the circuit design and components for making this module intrinsically safe.

FIG. 3 shows a schematic diagram illustrating example features of a laser diode driving current module 300 consistent with the system 100 shown in FIG. 1, and circuit design and components that can be used to make such a module intrinsically safe consistent with implementations of the current subject matter. A laser diode 302 can reside in the hazardous area 104, and a laser diode protecting circuit 304 can reside in the non-hazardous area 108. The laser diode protecting circuit 304 can limit or reduce (or, in some implementations of the current subject matter, monitor and limit or reduce) the current and voltage at an output circuit branch 390 that can be fed into the laser diode 302. Providing a low and controlled current and voltage at the output circuit branch 390 to the laser diode 302, without risk of spiking, can enable the laser diode 302 to qualify as intrinsically safe. Safety components, which can include an active power limiting circuit 340, zener diodes 314, and first resistors 311, among other possible structures or approaches, can be strategically connected within the laser diode protecting circuit 304.

The laser diode protecting circuit 304 can be configured such that currents and voltages within the laser diode protecting circuit 304 are maintained at a level that is intrinsically safe, and such that the laser diode protecting circuit 304 can perform one or more of monitoring, limiting, and reducing current and/or voltage at the output circuit branch 390 entering into the laser diode 302 (which is positioned on the hazardous area 104) employing one or more of the following measures or similar or equivalent approaches. A fuse 332 can cutoff current entering into the active power limiting circuit 340 in the event that a threshold current entering into the fuse 332 is surpassed. Additionally, the zener diodes 314 can limit the voltage at the output circuit branch 390, before it is provided to the laser diode 302. As zener diodes generally have a maximum voltage and current rating, optional additional voltage and current limiting measures, such as using the active power limiting circuit 340, may be advantageous.

The active power limiting circuit 340 can include current and voltage limiting circuits. The active power limiting circuit 340 can include one or a series of differential operational amplifiers 342, each connected to a second resistor 312, and in turn connected to a second transistor 344. FIG. 3 shows three differential operational amplifiers 342, but it will be understood that other numbers of differential operational amplifiers are also within the scope of the current subject matter. The differential operational amplifiers 342 in the active power limiting circuit 340 can perform in a similar manner to the differential operational amplifier in the current monitoring circuit 240. The laser diode protecting circuit 304 can employ the active power limiting circuit 340 to monitor and control voltages and currents within the active power limiting circuit 304 and also those applied to the laser diode 302. The current at the output circuit branch 390 is the same as that at a first branch 391, according to basic circuit analysis. Therefore, the current at the first branch 391 can be measured to monitor the current entering into the laser diode 302.

The first resistors 311 can include at least one current sensing resistor, which can be used to measure the current at the first circuit branch 391. A basic calculation can then yield the voltage at the first branch 391. This voltage from the first branch 391 can be an input into the differential operational amplifiers 342 of the active power limiting circuit 340. The differential operational amplifiers 342 can compare the voltage from the first branch 391 with the second input voltage that it receives. When the voltage from the first branch 391 becomes too high, the operational amplifiers 342 can provide a very small or no current into a second branch 392, through the second resistor 312, which in turn can cause a second transistor 344 to increase its resistive characteristics. The resistance across the second transistor 344 can reduce the voltage at the third branch 393. Therefore, as the voltage at the first branch 391 increases beyond a threshold, the active power limiting circuit 340 can cause the voltage at the third branch 393 to decrease. The threshold may be, for example, a minimum voltage capable of causing ignition energy sufficient to ignite a potentially combustible gas mixture in the hazardous area 104. The voltage at the third branch 393 can then be applied to the first transistor 316, and when the voltage at the third branch 393 reaches or surpasses a threshold, the first transistor 316 controls, limits, reduces or cuts off the current at the output branch 390, before it is fed into the laser diode 302. At this point, the zener diodes 314 can also limit the voltage at the output branch 390.

Figure 4:
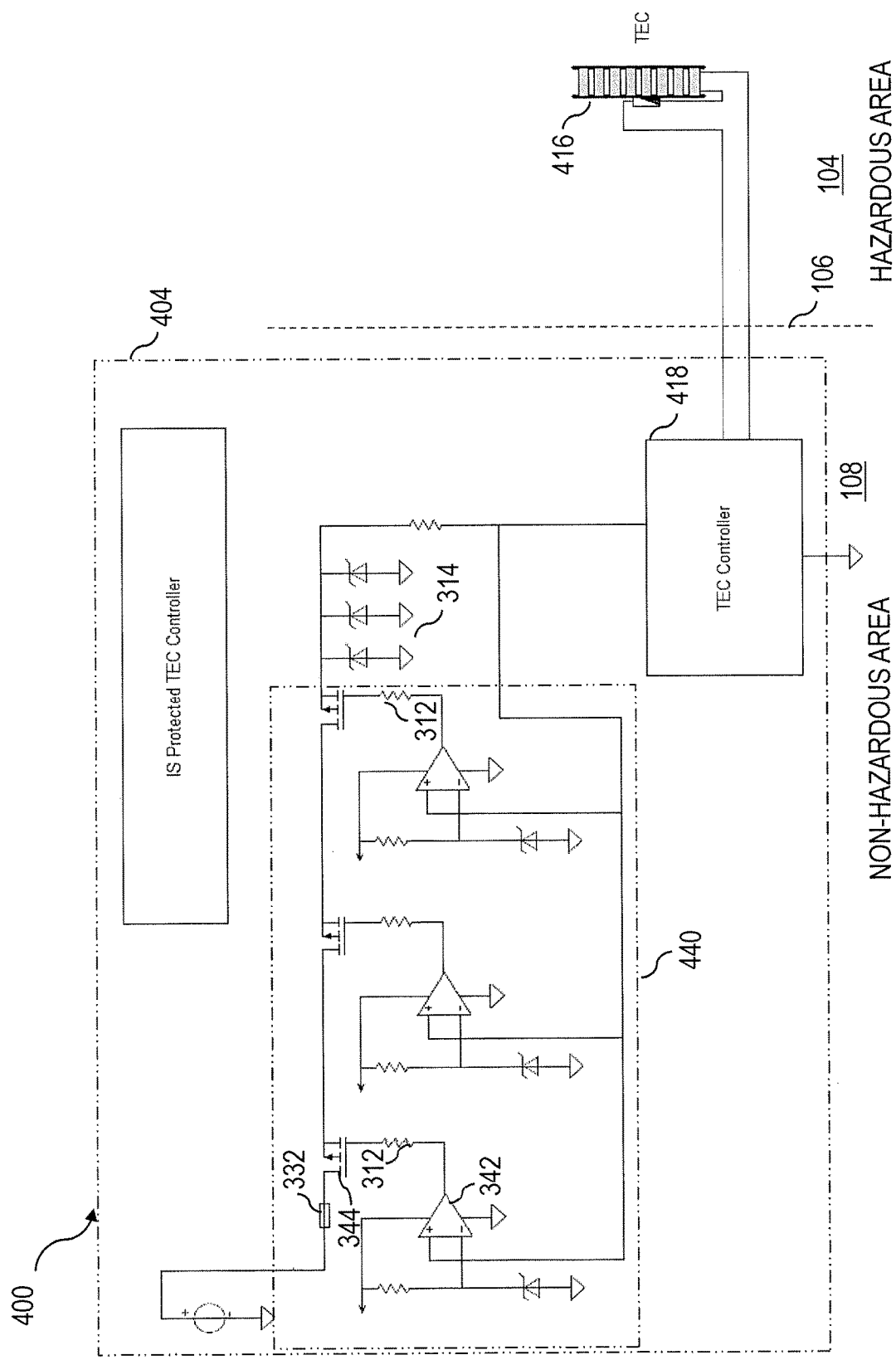
FIG. 4 shows a diagram illustrating examples of features of a protected thermoelectric cooler controller module that can be included in the system for analyzing samples of a reactive or potentially explosive gas or gas mixture, and the circuit design and components for making this module intrinsically safe.

FIG. 4 shows a schematic diagram illustrating example features of a cooling power module 400 consistent with the system 100 shown in FIG. 1, and circuit design and components that can be used to make such a module intrinsically safe consistent with implementations of the current subject matter. As discussed above, a module similar to the cooling power module 400 can be employed in a spectrometer for either or both of laser cooling and photodetector cooling. A thermal fuse 416 can reside in the hazardous area 104, and a cooling power module protecting circuit 404 can reside in the non-hazardous area 108. The thermal fuse 416 can be a separate series wired component mechanically close-coupled to the thermoelectric cooler controller 418, and can be used to prevent an over-temperature condition in the hazardous area 104. An active power limiting circuit 440 and zener diodes 314, can be safety critical measures strategically connected within the cooling power module protecting circuit 404. The active power limiting circuit 440 can optionally measure voltage or current in a similar manner to that described for the active power limiting circuit 340. The cooling power module protecting circuit 404 can use the active power limiting circuit 440 and the zener diodes 314 to perform one or more of monitoring, limiting, and reducing currents and/or voltages, optionally in a similar manner to that described for the laser diode protecting circuit 304 shown in FIG. 3, such that the cooling power module protecting circuit 404 and the thermoelectric cooler controller 418 can qualify as intrinsically safe. The thermal fuse 416 can provide an additional measure for monitoring a temperature in the hazardous area 106 and can provide a threshold temperature that can trigger the thermal fuse 416 to be set off. The threshold may be, for example, a minimum temperature capable of causing ignition energy sufficient to ignite a potentially combustible gas mixture in the hazardous area 104.

Figure 5:
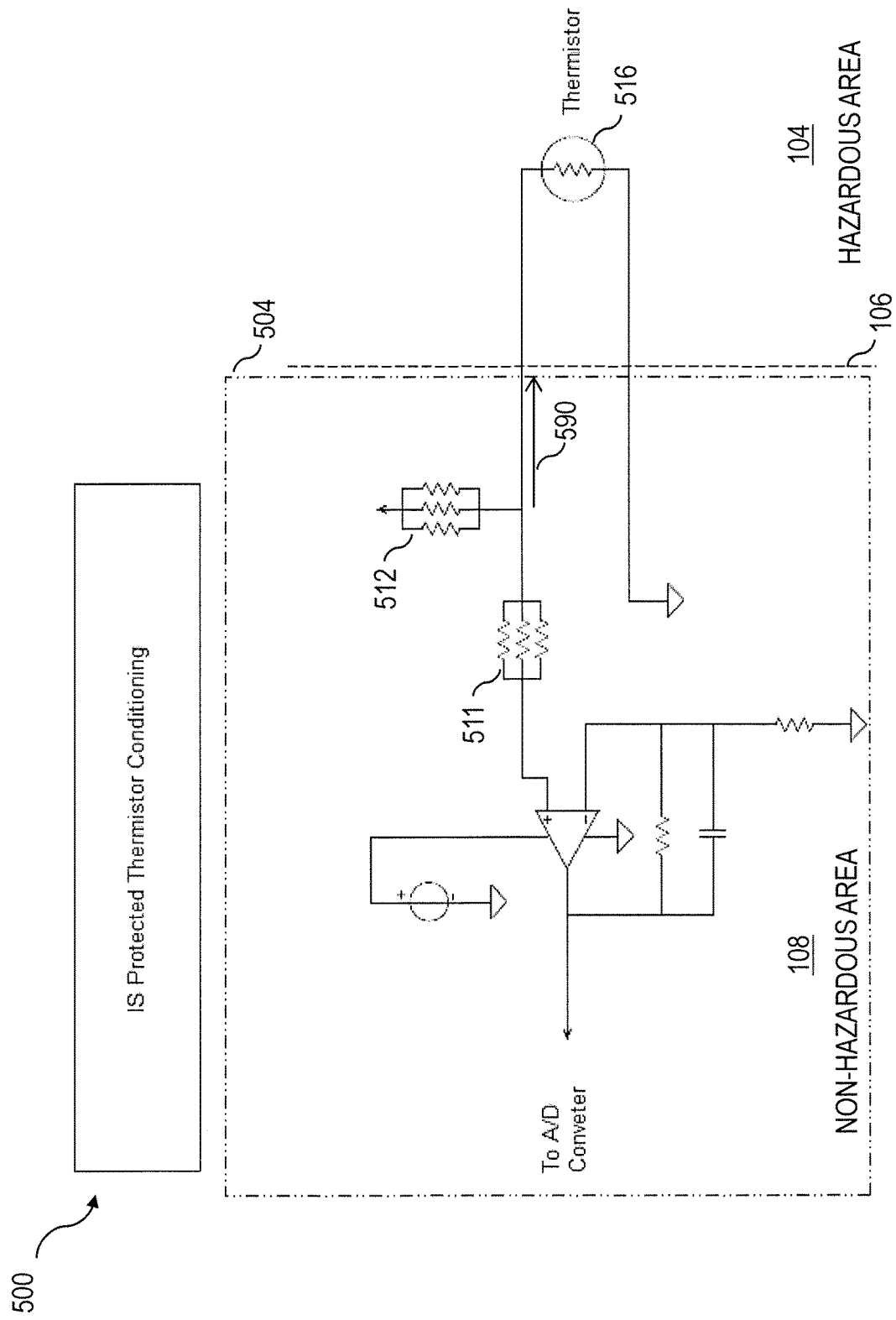
FIG. 5 shows a diagram illustrating examples of features of a protected thermistor conditioning module that can be included in the system for analyzing samples of a reactive or potentially explosive gas or gas mixture for a thermistor temperature sensor, and the circuit design and components for making this module intrinsically safe.

FIG. 5 shows a schematic diagram illustrating example features of a protected thermistor conditioning module 500 consistent with the system 100 shown in FIG. 1, and circuit design and components that can be used to make such a module intrinsically safe consistent with implementations of the current subject matter. As discussed above, a module similar to the protected thermistor conditioning module 500 can be employed in a spectrometer for temperature control of either or both of a laser and a photodetector. A thermistor conditioning module protecting circuit 504 can limit or reduce (or, in some implementations of the current subject matter, monitor and limit or reduce) voltages and/or currents using a first resistor 511 and a second resistor 512, which can be connected in the temperature monitoring module protecting circuit 504 as voltage dividers. The ratio of the resistances of the first resistor 511 and the second resistor 512 can control and adjust the voltage, and hence also the current on an output branch 590, before it is fed into a thermistor 516. Changing the values of one or another of the first resistor 511 and the second resistor 512 proportional to each other can change the voltage and current in the output circuit branch 590, such that the temperature monitoring module protecting circuit 504 and the thermistor 516 can qualify as intrinsically safe.

Figure 6:
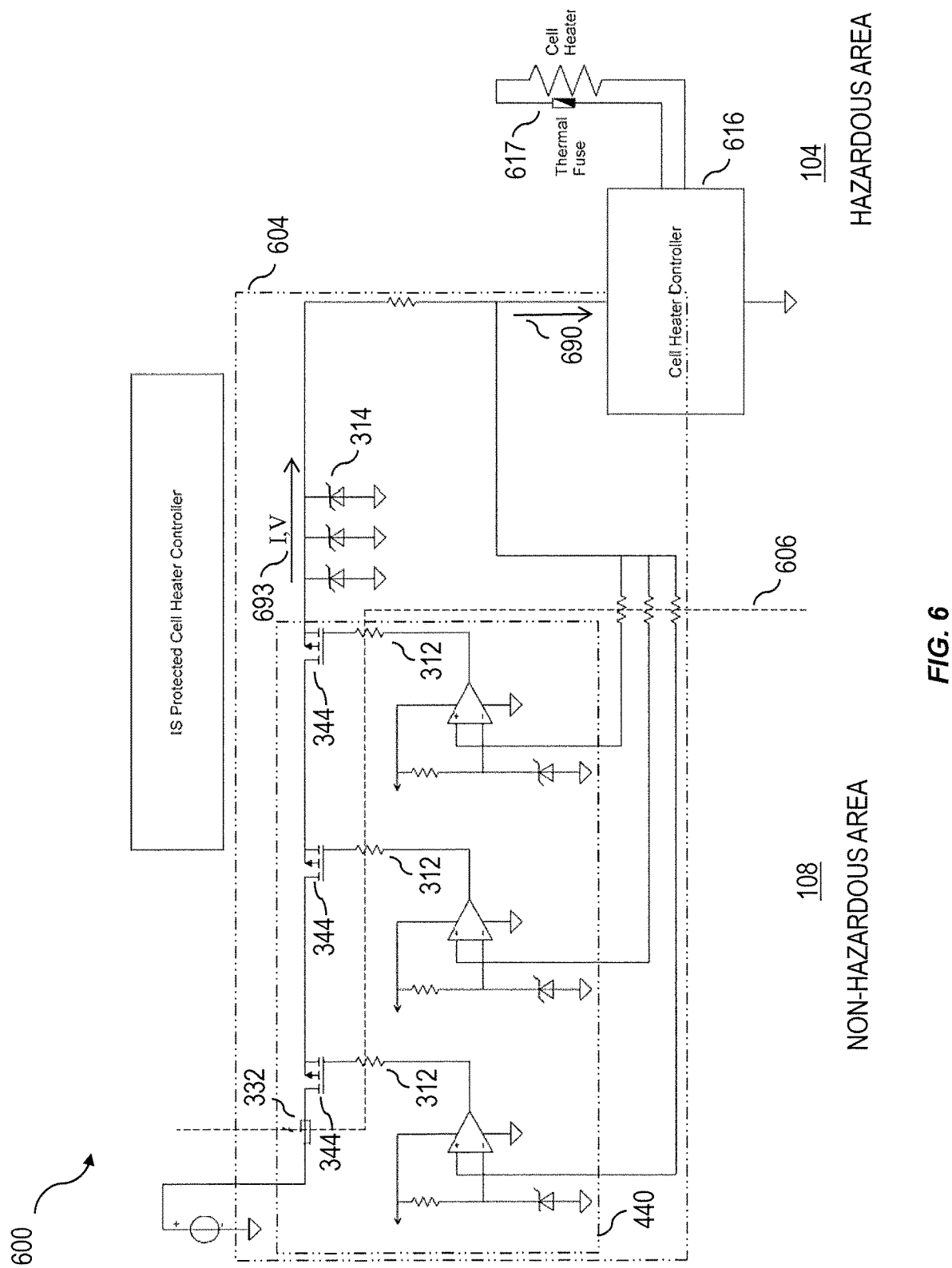
FIG. 6 shows a diagram illustrating examples of features of a protected cell heater controller module that can be included in the system for analyzing samples of a reactive or potentially explosive gas or gas mixture, and circuit design and components that can be used to make such a module intrinsically safe.

FIG. 6 shows a schematic diagram illustrating example features of a protected cell heater controller module 600 consistent with the system 100 shown in FIG. 1, and circuit design and components that can be used to make such a module intrinsically safe consistent with implementations of the current subject matter. A cell heater controller protection circuit 604 can be an intrinsically safe circuit design intended to keep a cell heater controller 616 connected to thermal fused coupled cell heater 617 intrinsically safe, by limiting power to these components. The circuit design of a cell heater protection circuit 604 can be similar to cooling power module protecting circuit 404 shown in FIG. 4. For example, the cell heater protection circuit 604 can include an active power limiting circuit 440 and zener diodes 314.

As an example, the physical barrier 606 separating the non-hazardous area 108 from the hazardous area 104 can be defined along, or can encase the fuse 332 and resistors 312. The cell heater controller 616, the zener diodes 314, the thermal fused coupled cell heater 617, and the transistors 344 from the power limiting active circuit 440 can reside in the hazardous area 104. The remainder of the cell heater controller protection circuit 604 can reside in the non-hazardous area 108.

The power limiting active circuit 440 can limit or reduce (or, in some implementations of the current subject matter, monitor and limit or reduce) the current and/or voltage at a third circuit branch 693. The zener diodes 314 can further limit the voltage at the third circuit branch 693 by limiting the voltage to not surpass a threshold voltage defined by the zener diodes 314. Providing a low and controlled current and voltage at the third circuit branch 693, and in turn at an output circuit branch 690 that is fed into the cell heater controller 616, without risk of spiking, can enable the cell heater controller 616 to qualify as intrinsically safe.

Figure 7:
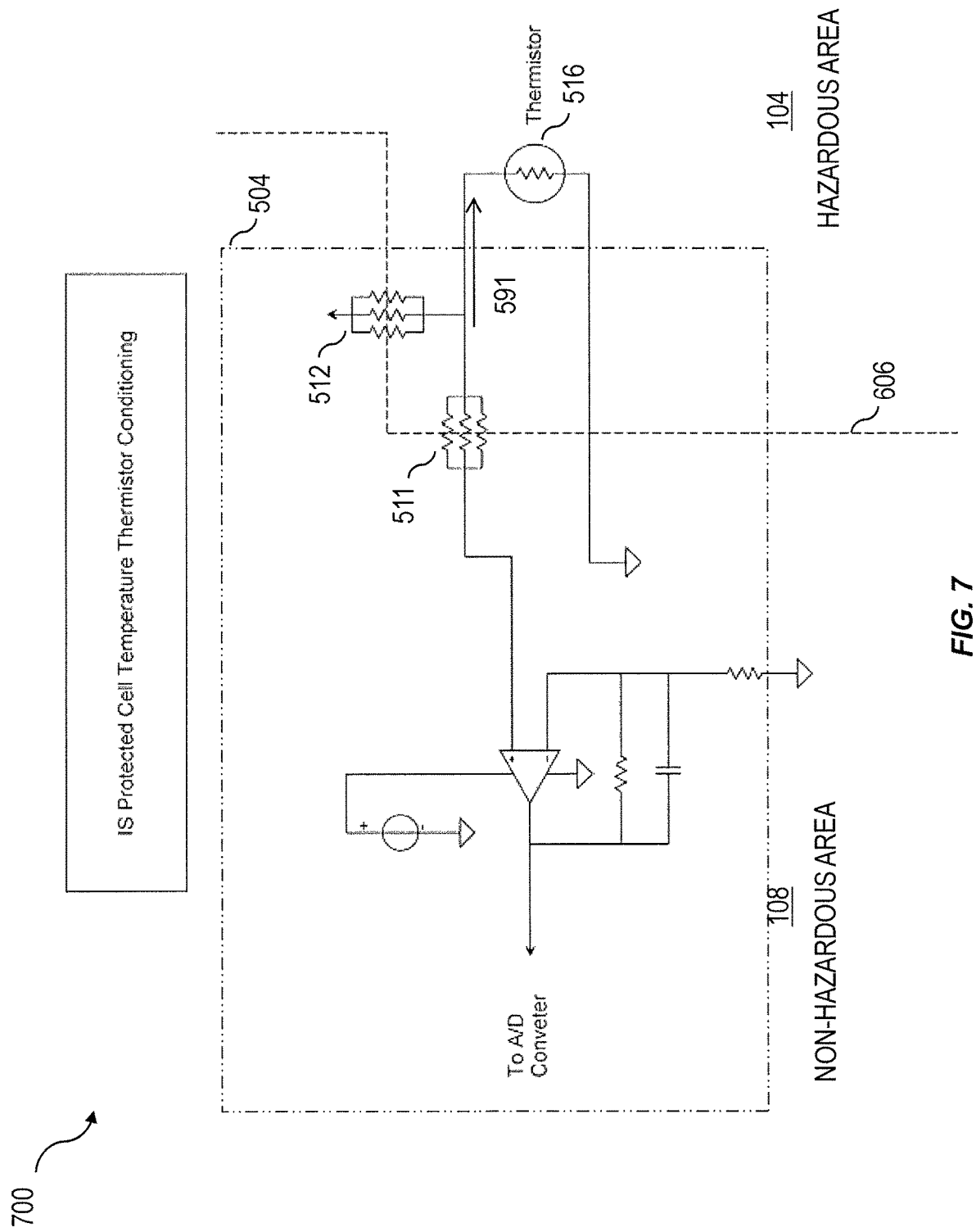
FIG. 7 shows a diagram illustrating examples of features of a protected cell temperature thermistor conditioning module that can be included in the system for analyzing samples of a reactive or potentially explosive gas or gas mixture, and circuit design and components that can be used to make such a module intrinsically safe.

FIG. 7 shows a schematic diagram illustrating example features of a protected thermistor conditioning module 700 with an alternative barrier implementation consistent with the system 100 shown in FIG. 1, and circuit design and components that can be used to make such a module intrinsically safe consistent with implementations of the current subject matter. The protected thermistor conditioning module 700 can include a thermistor conditioning module protecting circuit 504 similar to that shown in FIG. 5, which can be an intrinsically safe circuit design intended to keep the thermistor 516 intrinsically safe by limiting power to the thermistor 516. The physical barrier 606 separating the non-hazardous area 108 from the hazardous area 104 can be defined along, or can encase, the first resistor 511 and the second resistor 512.

Figure 8:
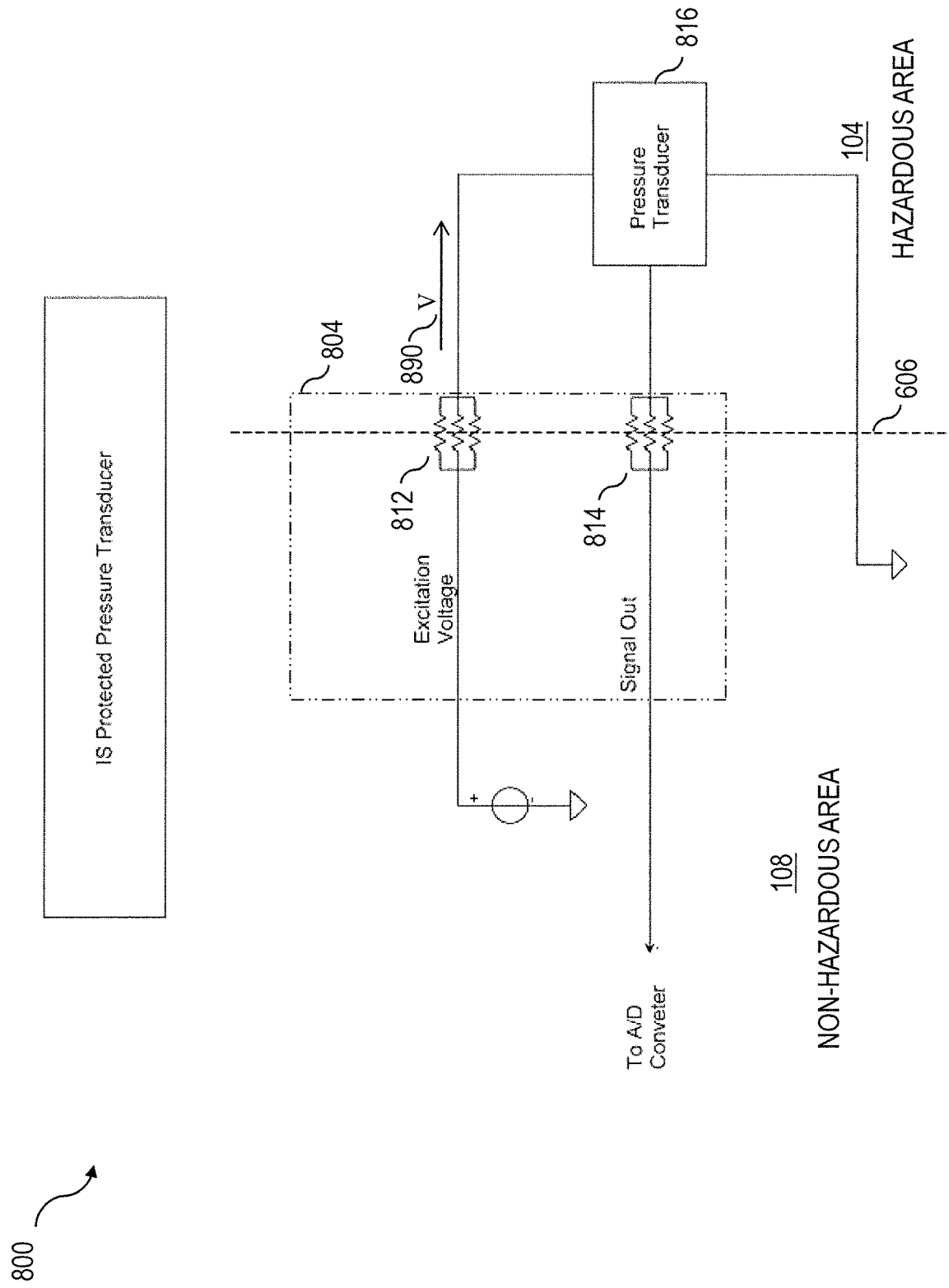
FIG. 8 shows a diagram illustrating examples of features of a protected pressure transducer module that can be included in the system for analyzing samples of a reactive or potentially explosive gas or gas mixture, and circuit design and components that can be used to make such a module intrinsically safe.

FIG. 8 shows a schematic diagram illustrating example features of a protected pressure transducer module 800 consistent with the system 100 shown in FIG. 1, and circuit design and components that can be used to make such a module intrinsically safe consistent with implementations of the current subject matter. A pressure transducer protecting circuit 804 can limit or reduce (or, in some implementations of the current subject matter, monitor and limit or reduce) voltages and/or currents using a first resistor 812 and a second resistor 814, which can be connected to a pressure transducer 816. The values of the first resistor 812 and a second resistor 814 can be varied such that a voltage drop across them, respectively, can result in providing an intrinsically safe pressure transducer 816. A physical barrier 606 between the non-hazardous area 108 and the hazardous area 104 can be defined along, or encase the first and second resistors 812 and 814. The first resistor 812 can cause a voltage drop at an output circuit branch 890, such that a controlled lowered voltage is fed into a pressure transducer 816, and can thereby cause the pressure transducer 816 to be considered as intrinsically safe. An additional voltage drop across resistor 814 can allow a lower voltage into the analog to digital converter.

Figure 9:
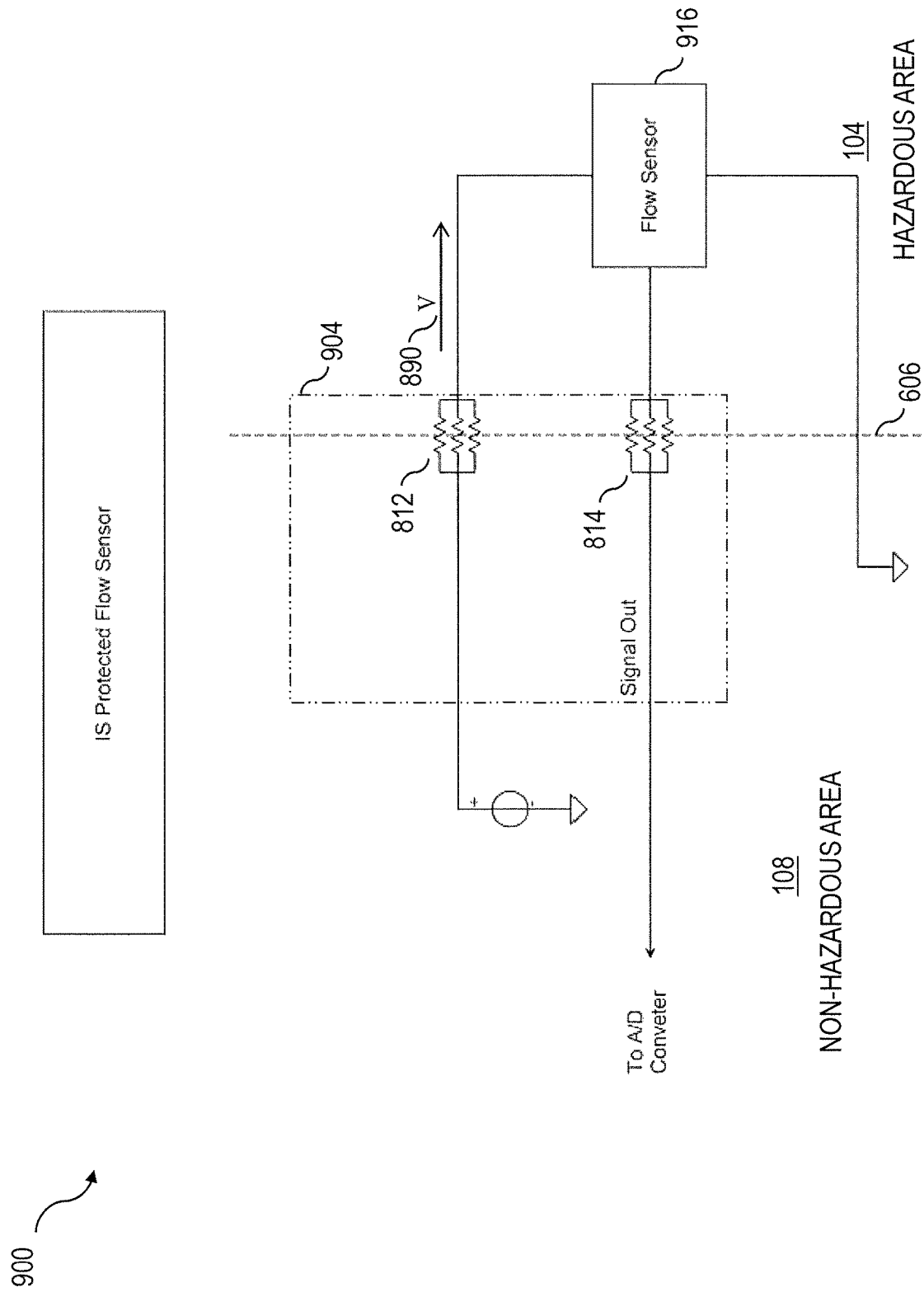
FIG. 9 shows a diagram illustrating examples of features of a protected flow sensor module that can be included in the system for analyzing samples of a reactive or potentially explosive gas or gas mixture, and circuit design and components that can be used to make such a module intrinsically safe.

FIG. 9 shows a schematic diagram illustrating example features of a protected flow sensor module 900 consistent with the system 100 shown in FIG. 1, and circuit design and components that can be used to make such a module intrinsically safe consistent with implementations of the current subject matter. A flow sensor protecting circuit 904 can be used to make a flower sensor 916 intrinsically safe. The flow sensor protecting circuit 904 can limit or reduce (or, in some implementations of the current subject matter, monitor and limit or reduce) voltages and/or currents in a similar manner to that described for the pressure transducer protecting circuit 804 of FIG. 8. In this example, the flow sensor is protected rather than the pressure transducer 816.

Figure 10:
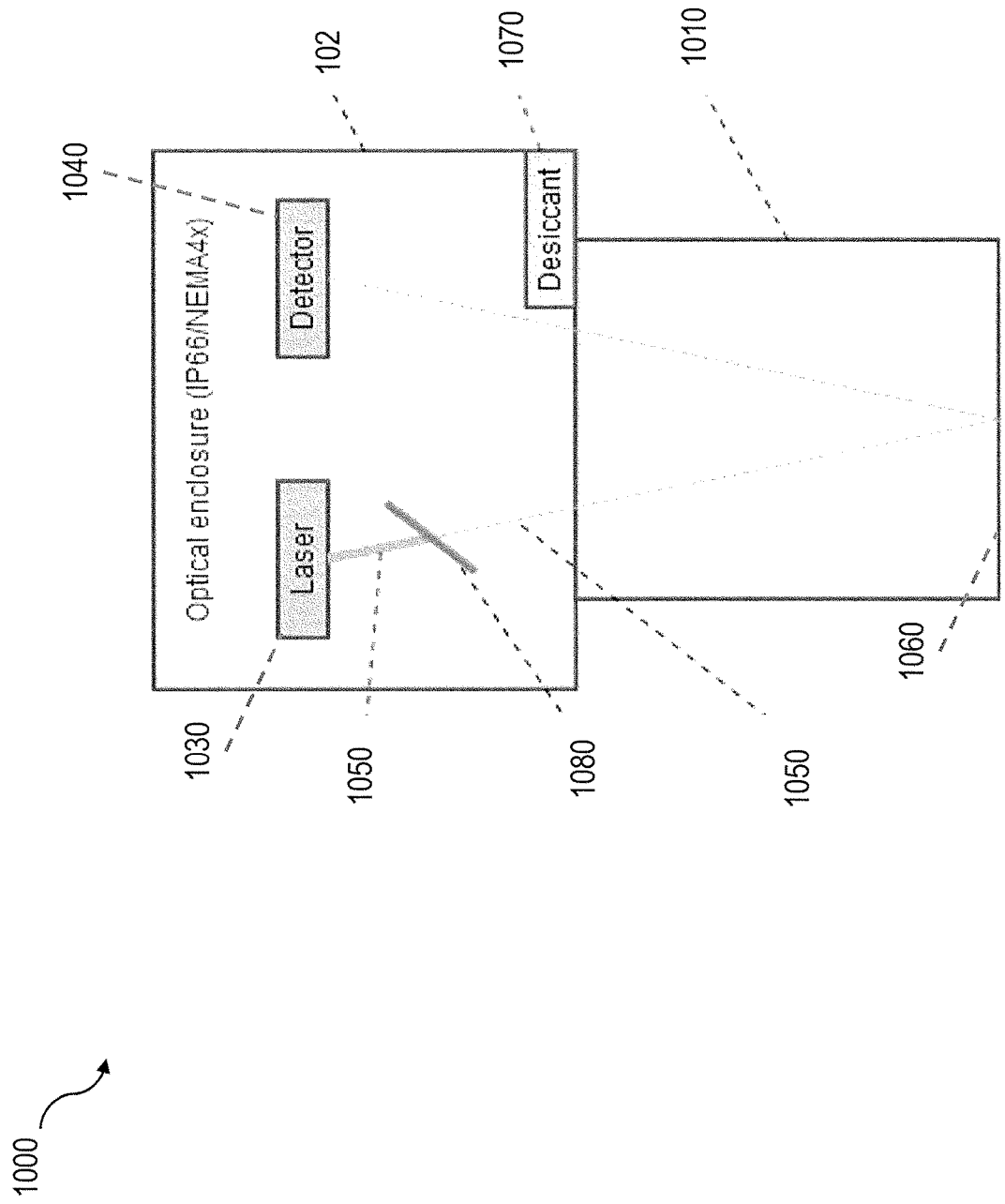
FIG. 10 shows a diagram illustrating examples of features of a spectrometer for limiting optical power delivery.

FIG. 10 shows a schematic diagram illustrating example features of a protected flow sensor module 900 consistent with the system 100 shown in FIG. 1, Various other implementations of the current subject matter can be used in order to limit the power provided the components of a laser spectrometer. For example, a ratiometric approach may be adopted, involving use of a ratiometric circuit (e.g., for the temperature thermistor and/or pressure transducer), in which the supply voltage would be directly proportional to an output voltage, as would be understood by a person of ordinary skill in the art. Further, fiber optic connections can be used for connecting components from the hazardous area to the non-hazardous area. For example, using fiber optics to connect the laser and to the photodiode.

Fiber optics can also be used for the delivery of the energy needed to operate the laser, the TEC, the photodiode and various other electronic circuitry. This can eliminate the need for electrical connectors which have a potential to spark. This can also facilitate a remote location for the sample cell, for example, directly on a pipeline or on a tank, while the main controller and other data processing electronics can be located in a general purpose area, or an area which only requires a lesser certification, for example Div2/Zone2 certification. Fiber-coupled high efficiency laser diodes can also be used. These can including commonly available 980 nm EDFA pump lasers which can deliver the 980 nm light by means of a suitable optical fiber to the tunable diode laser sample cell. At the sample cell, the light delivered by fiber optic cable can be converted into electricity, using a photodetector operating similarly to a solar cell. The driving laser can be located in the main controller unit or be a separate accessory. Connections can be made via fiber connectors, instead of with electrically conducting connectors. Multiple 980 nm or other lasers can be fiber-combined to scale up the total power delivered. If the fiber cable is broken or damaged, the power provided to the laser spectrometer can be automatically cut off, in order to comply with safety requirements.

In another approach consistent with implementations of the current subject matter, digital signals transmitted by fiber-optic connections can be utilized for communications between the optical head 102 and the micro-controller 112. Such an approach can eliminate at least some of the electrical wiring typically required in a modem spectrometer, as well as the associated risks of spark hazards, the requirements for enclosing wires in conduits, the need for circuitry to comply with electromagnetic compatibility (EMC) requirements, and potential concerns about robustness of circuits against electro-magnetic radiation. In other implementations of the current subject matter, use of wireless radio communications (e.g. via bluetooth, WiFi, and possible future wireless protocols) for data transfer can also eliminate or reduce at least some of the explosion risks associated with spectrometer circuitry.

Furthermore, an intrinsically safe sample cell with the laser, the TEC, the photodetector and the electronic circuitry can be operated directly from a small solar panel attached to the sample cell or mounted closely thereto. High efficiency flexible solar cells are available and can be tailored to work within such a spectrometer implementation. In some implementations of the current subject matter, one or more solar cells can be incorporated with a backup battery to allow continuous operation of the spectrometer even if the solar power only is temporarily insufficient.

In some implementations of the current subject matter, an intrinsically safe, explosion proof approach to laser spectroscopy can include measures that prevent a laser beam from achieving sufficient power delivery to be capable of igniting an explosion. Three potential ignition mechanisms generally need to be considered. First, optical radiation (e.g. from a semiconductor laser or other laser light source) can be absorbed by a potentially explosive gas mixture and cause ignition of the mixture either due to a local temperature rise or due to photochemical processes. Second, absorption of laser radiation by solid surfaces or particles can lead to ignition of a potentially explosive gas mixture with continuous wave radiation in the near infrared and/or visible spectral ranges. Third, pulsed, focused laser radiation can under some conditions cause formation of a plasma or cause a reaction at the absorber surface, and thereby cause ignition.

FIG. 10 shows a diagram of an example spectrometer configuration 1000 in which a cell 1010 may contain a potentially explosive gas mixture and may also contain particles. The spectrometer 1000 also includes an optical head 102, which can contain a laser 1030 and a detector 1040. Laser radiation 1050 from the laser 1030 can pass from the optical head 102 to the cell 1010 (e.g. via a window, not shown) and can optionally be reflected one or more times in the cell 1010 (e.g. on one or more reflectors or mirrors 1060) before reaching the detector 1040 (which does not necessarily need to reside in the optical head 102 or in the same optical head 102 as the laser 1030 although it is shown that way in FIG. 10).

In currently available solutions for a laser spectrometer in or near which a potentially explosive gas mixture may be present, an optical head 102 is generally implemented as an explosion proof housing capable of containing an explosion. Such enclosures are generally bulky, heavy, and expensive. As an alternative, consistent with implementations of the current subject matter, an enclosure for the optical head 102 can be sealed hermetically to prevent the build-up of an explosive atmosphere inside the optical head. The design implications for such an approach are similar to the ones described above for the explosion proof housing. Another approach is to exclude any potentially explosive gas mixtures from intersecting with the laser beam 1050, either inside a spectrometer cell or in passing between the laser 1040 and the cell 1010.

One or more implementations of the current subject matter can include avoidance of potential ignition mechanisms in a spectrometer cell 1010 capable of containing a potentially explosive gas mixture and can therefore allow construction and use of such a spectrometer 1000 without requiring an explosion-proof enclosure for the optical head 102. In general, limiting the optical power to less than a safety threshold (e.g. approximately 35 mW or approximately 5 mW·mm-2) and/or ensuring that no particles are present in the path 1050 of the laser radiation can ensure that ignition due to the laser radiation is not possible. Particles can be potentially problematic ignition sources in that their small mass can lead to highly elevated surface temperatures when particles interact with (e.g. absorb radiation from) a laser beam.

While it is possible to design a spectrometer 1000 in which the optical power output of a laser source (e.g. a semiconductor laser or the like) does not exceed the safety threshold (e.g. approximately 35 mW) under normal operating conditions, because laser power output from a semiconductor laser can be dependent on both the laser driving current and the laser temperature (increasing drive current and/or decreasing operating temperature generally result in increasing laser power output), there are feasible circumstances in which a fault or other malfunction in one or more control circuits or even in a microprocessor 112 of the spectrometer (or alternatively, user error or deliberate misuse) could result in significantly excess laser driving current being delivered and/or an operating temperature of the laser 1040 being much lower than intended. Either of these factors (or both in combination) as well as other potential factors which are not excluded by the current description have the potential to result in significantly increased laser power output, possibly in excess of the safety threshold.

Consistent with implementations of the current subject matter, an optical head 102 can be manufactured in an environment which is considered particle free. A particle excluding (e.g. consistent with an IP66/NEMA4x rating) enclosure around the optical head 102 can prevent particles from entering the optical head 102 during "in the field" use of the spectrometer 1000. This kind of an enclosure can be much easier/cheaper to build and less bulky and/or expensive than an explosion proof housing.

Inside an optical head 102 in which particles are excluded, the optical power can safely exceed the safety threshold (e.g. as illustrated by the thicker line near the laser 1040 in FIG. 10) because there are no particles inside which could cause an explosion by absorbing the optical power. If the interior volume of the optical head 102 or its enclosure includes a desiccant 1070 that must be serviceable in the field, the desiccant 1070 can optionally be placed in its own compartment in the optical head 102, and this compartment can be separated from a main compartment containing the laser by a membrane which is permeable to water vapor (e.g. so that the desiccant can efficiently keep the moisture levels in the enclosure at a low level) but not particles. In this manner, the membrane can prevent particles from entering the part of the optical head 102 where the laser beam path 1050 passes when the desiccant 1070 is replaced or serviced. In other implementations of the current subject matter, a desiccant that is not friable, or that otherwise does not create airborne particles, can be used, thereby obviating a need for a separate compartment for the desiccant.

Also consistent with implementations of the current subject matter, the cell 1010 within which the gas mixture is contained or through which a gas stream passes need not be a critical component in explosion safety. Incorporation of one or more optical head features discussed herein can guarantee that the optical power in the cell will under no circumstances exceed a safety threshold (e.g. the aforementioned 35 mW), thereby allowing for a cell design which does not need to include any specific explosion protection mechanisms. As a result, the cell 1010 can be lighter and the whole design can be fully focused on measurement performance (e.g. ensuring that extraneous factors do not interfere with an accurate measurement and quantification of one or more analytes in a gas mixture or gas stream being analyzed using a spectrometer). For example, as a spectrometer 1000 incorporating various features discussed herein does not require flame arresters or other similar devices in gas piping or routing channels (e.g. passages that deliver gas to and remove gas form the cell 1010) to prevent an explosion within the cell 1010 from propagating, cost can be reduced, and measurement performance can be improved. For example, a flame arrester may retain one or more analytes via an absorption or adsorption mechanism, thereby slowing the responsiveness of the spectrometer to changes in the composition of a gas stream being analyzed. Elimination of a need for such features of a spectrometer can be beneficial.

To achieve a restriction of the optical power delivered to the cell 1010 of a spectrometer 1000 to lower than a safety threshold (e.g. less than approximately 35 mW of optical power), one or more additional features may be implemented in the optical head 102. In some implementations, electrical power to the laser can be restricted to less than a prescribed amount of current. One approach to imposing this restriction can be an intrinsically safe protected laser drive circuit such as that described above in reference to FIG. 3. Other approaches to clamping the voltage supplied to the laser and thereby limiting the current can also satisfy this requirement without necessarily providing an intrinsically safe circuit.

Active monitoring of the optical power from the laser can be implemented to reduce the electrical power dynamically if the laser power gets close to the safety threshold. As an alternative, one or more optical filters 1080, such as for example a neutral density (ND) filter, a tunable wavelength filter (e.g. a fiber Bragg grating, an interference filters, a tunable MEMS transmission filter, or the like), etc. can be employed to reduce the optical power delivered to the cell to less than the threshold. Such an optical filter 1080 can be advantageously dimensioned such that the optical filter 1080 effectively reduces the optical power to less than the safety threshold under both regular operating conditions and "worst case" conditions, examples of which may be runaway laser drive circuits, user error or deliberate misuse, over-cooling of the laser, etc. As shown in FIG. 10 and mentioned above, the optical filter 1080 in this example can be positioned some distance away from the laser 1030 if the optical head 102 is particle free—excess laser power (e.g. above the safety threshold) is incapable of igniting a gas mixture without a surface or some other medium such as particles that are capable of absorbing the laser energy.

In some implementations, it can be advantageous to implement an additional thermal shut-off for the laser 1030. Since the laser becomes more efficient at low temperatures (lower than the regular operating temperature set point), it could exceed the prescribed optical power limits if its temperature gets too low. Again, such limits can be implemented by means of an active optical power monitoring of the laser, which is capable of reducing the electrical energy provided to the laser when the optical power approaches the safety threshold. As an alternative, the laser 1030 can be shut-off or the electrical power to the laser reduced by monitoring the temperature only. Various approaches to achieve this feature are within the scope of the current disclosure, including but not limited to use of an electrical device with a negative temperature coefficient in series with the laser, use of an electrical device with a positive temperature coefficient in parallel to the laser, use of active temperature monitoring which senses the temperature and shuts off the laser/reduces its power when the temperature gets too low, and the like.

For the example of an electrical device with a negative temperature coefficient in series with the laser, the resistance and thus the voltage drop across such a device increases as the temperature decreases. With a proper dimensioning of such a device and the fact that the voltage to this circuit is clamped, the voltage across the laser will drop below the threshold voltage when the temperature gets too low, thereby reducing its optical power. In one example extreme case, the device can be a thermal switch (e.g. a bimetal switch), which opens its contact then the temperature gets too low.

For use of an electrical device with a positive temperature coefficient in parallel to the laser (in one example a switch like a bimetal), such a device generally reduces its resistance when the temperature drops. Such a drop in resistance can effectively shunt the laser and reduce the current through the laser which reduces the optical power.

Active temperature monitoring for sensing the temperature and shutting off the laser and/or reducing its power when the temperature gets too low can be implemented in some examples by adding a device in series with the laser. This device can be controlled to increase its resistance and/or open a contact (e.g. an analog switch or a tunable resistor) or by adding a device in parallel to the laser which is controlled to reduce its resistance/close a contact (e.g. an analog switch or a tunable resistor) to reduce the current through the laser.

Depending on the protection level of the device, two or more of the mechanisms described above (or others) can be combined to achieve a protection with single or multiple homogeneous or heterogeneous redundancy.

To enable effective spectroscopy while also provide intrinsic safety for a laser spectrometer, one or more design tradeoffs may be required. For example, the optical power provided from the laser 1030 to a gas mixture in the cell 1010 may necessarily be capped below the safety threshold (e.g. 35 mW) using one or more of the approaches described above while ensuring that sufficient laser power can be provided to ensure that a signal received at a detector of the spectrometer supports any desired spectroscopic analysis. Design parameters can include consideration (and mitigation) of a worst case for maximum optical power (e.g. under failure or misuse conditions) in which a lowest ambient temperature (e.g. an environmental temperature where the spectrometer system is related being used) for which the spectrometer system is related occurs and a TEC control/drive failure also occurs such that the TEC cools at maximum power based on the limits of the IS circuit (e.g. one similar to that described above in reference to FIG. 4 and/or FIG. 5). Such a case can result in very low temperatures for the laser where it reaches it maximum efficiency. A further feature of the "worst case" scenario would be a maximum laser drive current based on the limits of the IS circuit (e.g. one similar to that described above in reference to FIG. 3). In general, the absolute limit for the worst case laser power can be based on the electrical power capable of being provided to the laser and the quantum efficiency of the laser. The real values for typical lasers in use in spectrometers may be lower than the maximum theoretical power, but defining the theoretical upper limit is a good exercise for ensuring safety under all possible conditions.

The laser power limiting features also need to take into account a worst case for minimum optical power at the detector (e.g. under operating conditions) to ensure usability over all condition ranges. This worst case is defined by the laser operating at its typical temperature set point (e.g. about 35° C. to 50° C.), a laser drive (e.g. mid point) as required for the spectroscopy approach of interest, any optical reflectors being obscured by some amount of dirt or other film that affects reflectance, and a gas mixture in the cell having a very strong absorbance at the target wavelength or over a wavelength scan range of interest. In general, within the constraints imposed by requirements to be intrinsically safe, the laser is advantageously scoped to allow usable spectroscopic signals at the detector over a largest range possible.

Providing intrinsically safe designs using electrical circuit designs, fiber optics, or solar cells, amongst other things, can provide advantages in the operation of a spectrometer. For example, they can allow for less constraints on the optical components that reside in the transition region between the "safe" area and the "hazardous area." Additionally, they can remove, or loosen the requirement for the optical measurement components to be part of an explosion-proof physical barrier. Additionally, constraints on the mechanical connections between the hazardous and the safe area can also loosen. The explosion proof barrier optionally need not be a precision machined part. Furthermore, the metal housing encasing the spectrometer may not have to be explosion-proof. All these advantages can offer direct cost, and thermal management benefits.

Moreover, intrinsically safe configurations for spectrometry-based analyzers consistent with implementations of the current subject matter can also provide benefits for thermal management. If a circuit is not implemented in an intrinsically safe manner, the electronic components that pose a risk of combustion may be encapsulated in an explosion proof box, thereby representing a single domain for thermal management. Alternatively, multiple explosion proof boxes can be used to encase individual components. However, the cost of this implementation may be prohibitive in most applications. By implementing an intrinsically safe design, the highly temperature sensitive part of the circuitry (mainly the laser) can be placed in a low-cost housing which does not need to be explosion proof because the circuits are intrinsically safe. This arrangement can allow for a thermal management implementation, which can split the highly sensitive thermal domain of the optics module from the less sensitive domain of the remaining electronics, which can remain in an explosion proof box.

Intrinsically safe designs consistent with those described herein can allow for a less rigorous optical window mounting, which does not require a flame or an explosion seal. For example, sample cells for natural gas and hydrocarbon applications can typically require a stainless steel construction considering the different thermal expansion coefficients between stainless steel, 15.6 ppm/K and typical window materials used in an optical spectrometer. For fused silica the difference is 15 ppm/K; for Bk7 it is at least 7 ppm/K; and for ZnS (zinc sulfide), ZnSe (zinc selenide), and sapphire it is at least 8 ppm/K. A typical infrared tunable diode laser spectrometer operates in the 760 nm to 10,000 nm wavelength range, where the use of BK7 and/or fused silica and/or sapphire and/or ZnS and or ZnSe windows can be advantageous.

Additionally, intrinsically safe designs consistent with the descriptions herein can allow for fewer robustness constraints to be required for optical windows, thereby allowing the use of different materials to design higher quality optical windows without requiring that they be explosion proof. For example, the non-negligible differential coefficient of thermal expansion between the sample cell window and the mounting material can distort the window due to the stress and strain resulting from the ambient or sample gas temperature changes. These optical window distortions can lead to erroneous concentration computation, amongst other things.

Figure 11:
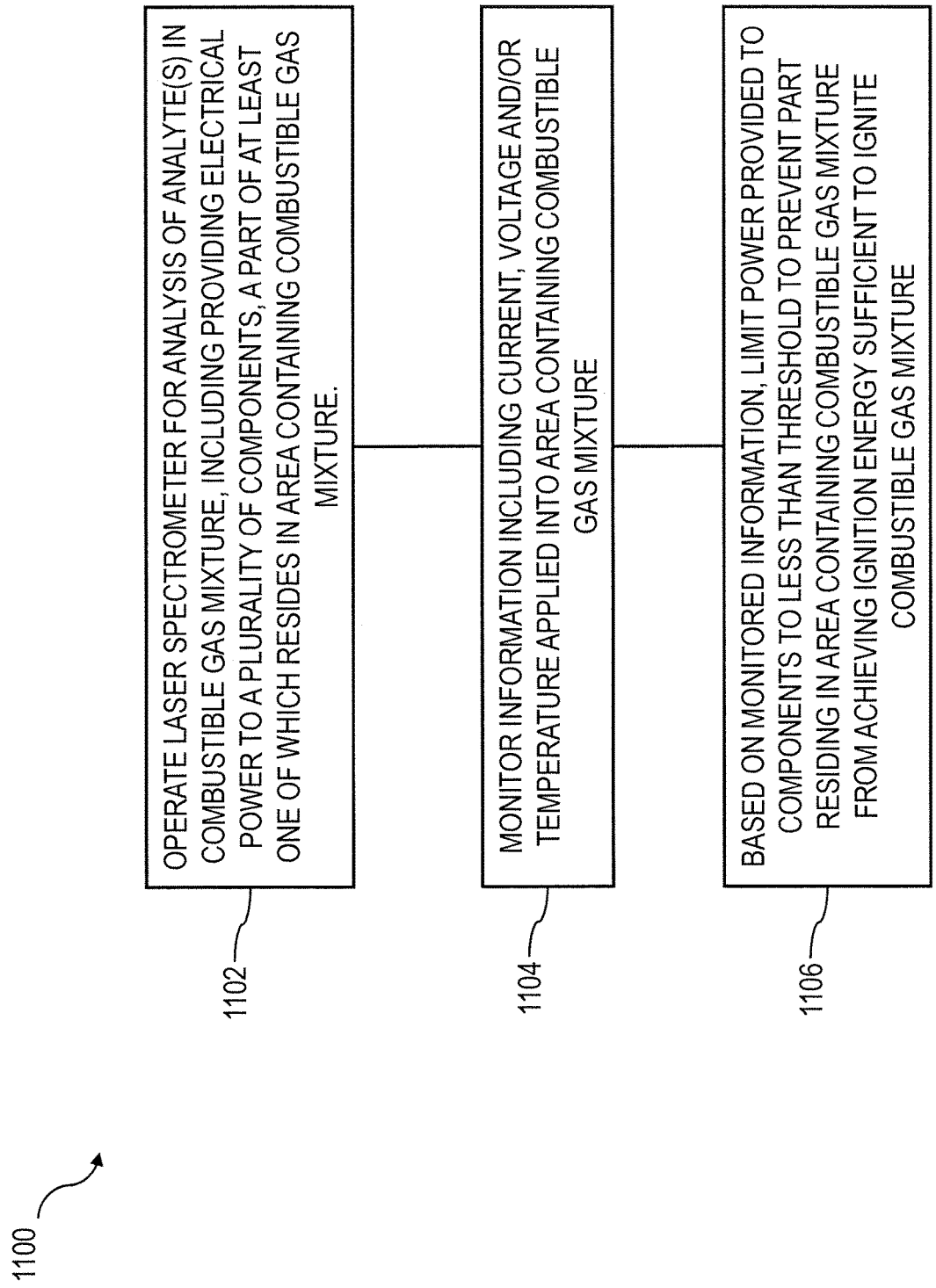
FIG. 11 shows a process flow diagram illustrating aspects of an example method having one or more features consistent with implementations of the current subject matter.

FIG. 11 shows an example process flow chart 1100 illustrating features of a method consistent with implementations of the current subject matter. At 1110, a laser spectrometer is operated for analysis of one or more analytes present in a mixture containing at least one combustible gas. The operating includes providing electrical power to a plurality of components (e.g. the various modules discussed above in reference to FIGS. 1-9) and optical power from a laser to a volume of the mixture (e.g. as discussed above in reference to FIG. 10). A hazardous area part of at least one of the plurality of components residing in a hazardous area of the spectrometer that may contain the mixture and that does not include at least one explosion mitigating structure.

At 1120, an optical power, electrical, electronic, and/or thermal ignition-causing parameter of the hazardous area part is limited to less than a safety threshold to prevent occurrence of an ignition energy sufficient to ignite the combustible gas mixture. The optical power, electrical, electronic, and/or thermal ignition-causing parameter includes one or more of the optical power delivered from the laser to the volume of the mixture, an amount of particles exposed to radiation from the laser that has not been optical power limited, a current provided to the hazardous area part, a voltage provided to the hazardous area part, a temperature of the hazardous area part, and a stored energy of the hazardous area part.

At 1130, the optical power, electrical, electronic, and/or thermal ignition-causing parameter is not limited for a non-hazardous area part of the at least one of the plurality of components. The non-hazardous area part resides in a non-hazardous area of the spectrometer that either cannot contain the mixture or that includes the at least one explosion mitigating structure.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A method comprising:
    operating a laser spectrometer for analysis of one or more analytes present in a mixture containing at least one combustible gas, the operating including providing electrical power to a plurality of components and optical power from a laser to a volume of the mixture, at least one of the plurality of components residing in a hazardous area of the spectrometer that contains the mixture and that does not include at least one explosion mitigating structure, and a protecting circuit portion of the at least one of the plurality of components residing in a non-hazardous area of the spectrometer;
    limiting an optical power, electrical, electronic, or thermal ignition-causing parameter to the hazardous area to less than a safety threshold using the protecting circuit portion to prevent occurrence of an ignition energy sufficient to ignite the combustible gas mixture, the optical power, electrical, electronic, and/or thermal ignition-causing parameter comprising one or more of the optical power delivered from the laser to the volume of the mixture, an amount of particles exposed to radiation from the laser, a current provided to the hazardous area, a voltage provided to the hazardous area, a temperature of the hazardous area, and a stored energy of the hazardous area;

providing a worst case specification for the optical power emitted from the laser; and turning off the laser when the operating conditions, including optical power measurement, indicate that the optical power from the laser will exceed the safe limits as set forth in the worst case specification.

2. A method as in claim 1, wherein the limiting comprises monitoring, via the protecting circuit portion, at least one of the optical power, the current, the voltage, the temperature, and the stored energy provided to the hazardous area.

3. A method as in claim 1, wherein the plurality of components includes the laser, a photodetector, a temperature control device, a temperature sensor, a temperature thermistor, a pressure transducer, an optical power reduction device and a flow sensor.

4. A method as in claim 1, wherein the limiting comprises limiting the voltage provided to at least one of the plurality of components to less than a minimum voltage capable of causing the ignition energy.

5. A method as in claim 4, further comprising:
detecting, via the non-hazardous area, that the voltage provided to at least one of the plurality of components is greater than or equal to the minimum voltage; and
reducing, via the hazardous area, the voltage by triggering a transistor and/or an electronic and/or an electro-mechanical circuit to increase an effective resistance.

6. A method as in claim 4, wherein the limiting further comprises use of at least one of a clamping zener diode, a fuse, an active power limiting circuit including an operational amplifier, and a voltage divider.

7. A method as in claim 4, wherein the limiting further comprises use of a fuse, and wherein the fuse includes a thermal fuse operable to prevent an over-temperature condition in the hazardous area.

8. A method as in claim 1, wherein the limiting comprises limiting the current provided to at least one of the plurality of components to less than a minimum current capable of causing the ignition energy sufficient to ignite the combustible gas mixture.

9. A method as in claim 8, wherein the limiting of the current comprises monitoring the current using at least one of a current monitoring circuit, an active power limiting circuit, and a current sensing resistor.

10. A method as in claim 1, wherein the limiting comprises limiting a surface temperature of at least one of the plurality of components to less than a minimum temperature capable of causing the ignition energy sufficient to ignite the combustible gas mixture.

11. A method as in claim 1, further comprising:
detecting that at least one of the current, the voltage, and the temperature is greater than or equal to the threshold; and
reducing the detected at least one of the current, the voltage, and the temperature to an amount that is less than the threshold.

12. A method as in claim 1, wherein the limiting comprises reducing or cutting off voltage or current applied to at least one of the plurality of components.

13. A method as in claim 1, wherein the limiting comprises preventing power spikes using coupling capacitors and zener diodes to smooth current or voltage applied to at least one of the plurality of components.

14. A method as in claim 1, wherein limiting the optical power in the gas mixture comprises passing radiation from the laser through an absorptive and/or reflective optical filter that reduces the optical power to less than a safety threshold.

15. A method as in claim 1, comprising providing energy optically to the hazardous area via a fiber optic cable.

16. A method as in claim 1, wherein a fiber-coupled high efficiency laser diode provides and limits voltage or current to at least one of the plurality of components, and light delivered by a fiber optic cable is converted into electric power provided to the plurality of components.

17. A method as in claim 1, wherein the non-hazardous area further comprises a micro-controller for controlling one or more of the protecting circuit portion and the hazardous area.

18. A method as in claim 1, wherein the optical power, electrical, electronic, and/or thermal ignition-causing parameter comprises the optical power delivered from the laser to the volume of the mixture and the current and the voltage provided to the hazardous area.

19. A computer program product comprising a non-transitory machine-readable medium storing instructions that, when executed by at least one programmable processor, cause the at least one programmable processor to perform operations comprising:

operating a laser spectrometer for analysis of one or more analytes present in a mixture containing at least one combustible gas, the operating including providing electrical power to a plurality of components and optical power from a laser to a volume of the mixture, at least one of the plurality of components residing in a hazardous area of the spectrometer that contains the mixture and that does not include at least one explosion mitigating structure, and a protecting circuit portion of the at least one of the plurality of components residing in a non-hazardous area of the spectrometer;

wherein the laser is enclosed in a particle excluding enclosure;

monitoring a status of an optical power, electrical, electronic, or thermal ignition-causing parameter in or applied into the hazardous area via the protecting circuit portion residing in the non-hazardous area, the optical power, electrical, electronic, and/or thermal ignition-causing parameter comprising one or more of the optical power delivered from the laser to the volume of the mixture, an amount of particles exposed to radiation from the laser a current provided to the hazardous area, a voltage provided to the hazardous area, a temperature of the hazardous area, and a stored energy of the hazardous area;

limiting the optical power, electrical, electronic, and/or thermal ignition-causing parameter of the hazardous area to less than a safety threshold using the protecting circuit portion to prevent occurrence of an ignition energy sufficient to ignite the combustible gas mixture, the protecting circuit portion comprising protecting circuitry configured to receive an initial current from a power source of the laser spectrometer, the protecting circuit portion configured to limit the optical power, electrical, electronic, and/or thermal ignition-causing parameter provided to the hazardous area;

providing a worst case specification for the optical power emitted from the laser; and turning off the laser when the operating conditions, including optical power measurement, indicate that the optical power from the laser will exceed the safe limits as set forth in the worst case specification.

20. A computer program product as in claim 19, wherein the plurality of components includes the laser, a photodetector, a temperature control device, a temperature sensor, a temperature thermistor, a pressure transducer, and a flow sensor.

21. A laser spectrometer comprising:
an enclosed hazardous area configured to contain a potentially combustible gas mixture to allow analysis of one or more analytes present in the combustible gas mixture;
a plurality of components including a hazardous area of at least one of the plurality of components residing in the enclosed hazardous area that contains the combustible gas mixture and that does not include at least one explosion mitigating device, and a protecting circuit portion of the at least one of the plurality of components residing in a non-hazardous area of the spectrometer;
wherein a laser of the spectrometer is enclosed in a particle excluding enclosure; and
electrical hardware configured to perform operations including:
limiting an optical power, electrical, electronic, and/or thermal ignition-causing parameter of the hazardous area to less than a safety threshold using the protecting circuit portion to prevent occurrence of an ignition energy sufficient to ignite the combustible gas mixture, the optical power, electrical, electronic, and/or thermal ignition-causing parameter comprising one or more of the optical power delivered from the laser to the volume of the mixture, an amount of particles exposed to radiation from the laser a current provided to the hazardous area, a voltage provided to the hazardous area, a temperature of the hazardous area, and a stored energy of the hazardous area;
providing a worst case specification for the optical power emitted from the laser; and
turning off the laser when the operating conditions, including optical power measurements, indicate that the optical power from the laser will exceed the safe limits as set forth in the worst case specification.

22. A laser spectrometer as in claim 21, wherein the plurality of components includes the laser, a photodetector, a temperature control device, a temperature sensor, a temperature thermistor, a pressure transducer, and a flow sensor.

23. A laser spectrometer as in claim 21, further comprising a laser and an optical filter, and wherein the limiting includes limiting the optical power by passing optical radiation emitted by the laser through the optical filter prior to the optical radiation encountering gas that contains particles, the optical filter operable to limit the optical power of the optical radiation to less than a safety threshold sufficient to prevent occurrence of an ignition source exposed to the combustible gas mixture.

* * * * *